United States Patent [19]

Coleman, III et al.

[11] 4,452,914

[45] Jun. 5, 1984

[54] TITANIUM COMPLEXES AND CATALYSTS PREPARED THEREFROM

[75] Inventors: William M. Coleman, III, Lake Jackson; Morris S. Edmondson, Alvin, both of Tex.

[73] Assignee: The Dow Chemical Company, Midland, Mich.

[21] Appl. No.: 407,857

[22] Filed: Aug. 13, 1982

[51] Int. Cl.$^3$ .............................................. C08F 4/64
[52] U.S. Cl. ................................... 502/122; 502/124; 502/125; 502/126; 526/140; 526/141; 526/142; 526/125
[58] Field of Search ........... 252/429 B, 431 N, 431 R; 260/429.5

[56] References Cited

U.S. PATENT DOCUMENTS

| | | | |
|---|---|---|---|
| 2,795,553 | 6/1957 | Lowe | 260/429.5 X |
| 3,047,515 | 7/1962 | Piirma | 260/429.5 X |
| 3,134,737 | 5/1964 | Kay | 260/429.5 X |
| 4,082,692 | 4/1978 | Goldie | 252/429 B |
| 4,120,820 | 10/1978 | Birkelbach | 252/429 B |
| 4,180,636 | 12/1979 | Hirota | 252/429 B X |

OTHER PUBLICATIONS

Feld et al., *The Organic Chemistry of Titanium*, Pub. by Butterworths, Wash. D.C., (1965), pp. 63, 64, 73, 74, 78.
Yamamoto, A. and Kambara, S. K., "Chelate Compounds of Titanium with Salicylaldehyde and Methyl Salicylate", *J. Inorgan. Nucl. Chem.*, 1961, vol. 21, pp. 58–63.
Rosenhein, A., "Die Einwirkung von Titantetrachlorid auf Sauerstoffhaltige Organische Verbindungen", *Berichte der Deutschen Chemischen Gesellschaft*, 1915, pp. 447–452.
Funk, H., *J. Prakt. Chem.*, 1956, pp. 320–332.

*Primary Examiner*—Patrick Garvin

[57] ABSTRACT

Novel titanium compounds or complexes are prepared by reacting a titanium compound such as titanium tetraisopropoxide with a compound containing at least one aromatic hydroxyl group. These compounds and/or complexes are useful as the transition metal component in Ziegler-Natta catalysts.

75 Claims, No Drawings

TITANIUM COMPLEXES AND CATALYSTS PREPARED THEREFROM

BACKGROUND OF THE INVENTION

This invention relates to precursors for and to new catalyst compositions useful for initiating and promoting polymerization of α-olefins and to a polymerization process employing such catalyst compositions.

It is well known that olefins such as ethylene, propylene and 1-butene in the presence of metallic catalysts, particularly the reaction products of organometallic compounds and transition metal compounds, can be polymerized to form substantially linear backbone polymers of relatively high molecular weight. Typically such polymerizations are carried out at relatively low temperatures and pressures.

Among the methods of producing such linear olefin polymers, some of the most widely utilized are those described by Professor Karl Ziegler in U.S. Pat. Nos. 3,113,115 and 3,257,332. In these methods, the catalyst employed is obtained by admixing a compound of a transition metal of Groups IVB, VB, VIB, and VIII of Mendeleev's Periodic Table of Elements with an organometallic compound. Generally, the halides, oxyhalides and alkoxides or esters of titanium, vanadium and zirconium are the most widely used transition metal compounds. Common examples of the organometallic compounds include the hydrides, alkyls and haloalkyls of aluminum, alkylaluminum halides, Grignard reagents, alkali metal aluminum hydrides, alkali metal borohydrides, alkali metal hydrides, alkaline earth metal hydrides and the like. Usually, polymerization is carried out in a reaction medium comprising an inert organic liquid, e.g. an aliphatic hydrocarbon, and the aforementioned catalyst. One or more olefins may be brought into contact with the reaction medium in any suitable manner. A molecular weight regulator, which is normally hydrogen, is usually present in the reaction vessel in order to suppress the formation of undesirable high molecular weight polymers.

Following polymerization, it is common to remove catalyst residues from the polymer by repeatedly treating the polymer with alcohol or other deactivating agent such as aqueous base. Such catalyst deactivation and/or removal procedures are expensive both in time and material consumed as well as the equipment required to carry out such treatment.

Furthermore, most of the aforementioned known catalyst systems are more efficient in preparing polyolefins in slurry (i.e., wherein the polymer is not dissolved in the carrier) than in solution (i.e., wherein the temperature is high enough to solubilize the polymer in the carrier). The lower efficiencies of such catalysts in solution polymerization is believed to be caused by the general tendency of such catalysts to become rapidly depleted or deactivated by significantly higher temperatures that are normally employed in solution processes. In addition, processes involving the copolymerization of ethylene with higher α-olefins exhibit catalyst efficiencies significantly lower than ethylene homopolymerization processes.

Recently, catalysts having higher efficiencies have been disclosed, e.g., U.S. Pat. Nos. 3,392,159; 3,737,393; West German Patent Application No. 2,231,982 and British Pat. Nos. 1,305,610 and 1,358,437. While the increased efficiencies achieved by using these recent catalysts are significant, even higher efficiencies are desirable, particularly in copolymerization processes.

Even more recently, e.g. British Pat. No. 1,492,379, high efficiency catalysts have been employed which permit polymerization temperatures above 140° C. Such high polymerization temperatures provide for reduced energy requirements in solution polymerization processes in that the closer the polymerization temperature is to the boiling point of the polymerization solvent, the less energy that is required in removing the solvent.

The present invention provides for catalysts having higher efficiencies at these temperatures or higher polymerization temperatures at comparable efficiencies.

SUMMARY OF THE INVENTION

One aspect of the present invention pertains to titanium complexes and/or compounds resulting from reacting (A) at least one titanium compound represented by the formula $Ti(OR)_x X_{4-x}$ wherein each R is independently a hydrocarbyl group having from 1 to about 20, preferably from about 1 to about 10, most preferably from about 2 to about 4 carbon atoms; X is a halogen and x has a value from zero to 4; with (B) at least one compound containing at least one aromatic hydroxyl group represented by the formulas I, II, III, IV, V, VI, VII, VIII or IX;

wherein each A is independently a divalent hydrocarbyl group having from 1 to about 10, preferably from 1 to about 4, carbon atoms,

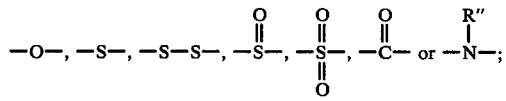

each A' is independently a divalent hydrocarbyl group having from 1 to about 10, preferably from about 1 to about 4, carbon atoms; each R is independently

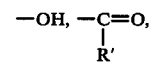

or a hydroxyl substituted hydrocarbyl or a hydroxyl substituted hydrocarbyloxy group having from 1 to about 20, preferably from 1 to about 10 carbon atoms; each R' is independently hydrogen, hydroxyl or a hydrocarbyl or hydrocarbyloxy group having from 1 to about 10, preferably from 1 to about 6, carbon atoms; each R" is independently hydrogen or a hydrocarbyl group having from 1 to about 10, preferably from 1 to about 6, carbon atoms; each X is independently a hydroxyl group, a nitro group, a nitrile group, a hydrocarbyl group, a hydrocarbyloxy group, a hydroxyl substituted hydrocarbyl or a hydroxyl substituted hydrocarbyloxy group each such groups having from 1 to about 20, preferably from 1 to about 12, carbon atoms or a halogen; m has an average value of from about 0.01 to about 6, preferably from about 1 to about 3; each n independently has a value of zero or 1; each x independently has a value of from zero to 2; each y independently has a value of from zero to 4, preferably from 1 to 2 and z has a value of from zero to 3, preferably from 1 to 2; and wherein components (A) and (B) are employed in quantities which provide a molar ratio of B:A of from about 0.1:1 to about 10:1, preferably from about 1:1 to about 4:1, most preferably from about 1:1 to about 2:1.

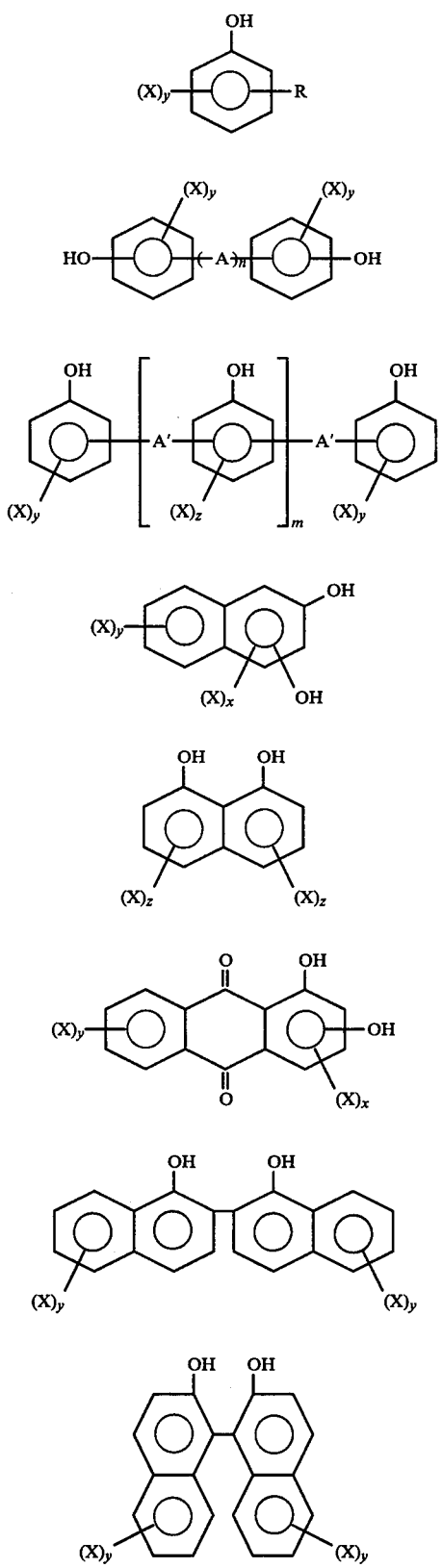

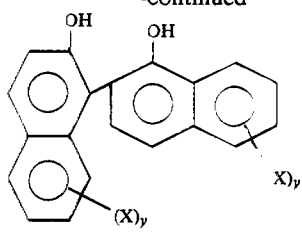

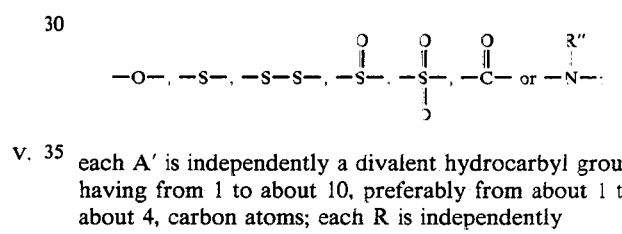

Another aspect of the present invention concerns an improvement in a Ziegler-Natta catalyst containing a titanium component wherein the improvement comprises employing as a titanium component, that which results from reacting (A) at least one titanium compound represented by the formula $Ti(OR)_xX_{4-x}$ wherein each R is independently a hydrocarbyl group having from 1 to about 20, preferably from 1 to about 10, most preferably from about 2 to about 4 carbon atoms; X is a halogen and x has a value from zero to 4; with (B) at least one compound containing at least one aromatic hydroxyl group represented by the formulas I, II, III, IV, V, VI, VII, VIII or IX;

wherein each A is independently a divalent hydrocarbyl group having from 1 to about 10, preferably from 1 to about 4, carbon atoms, $$-O-, -S-, -S-S-, -\overset{O}{\underset{}{S}}-, -\overset{O}{\underset{O}{S}}-, -\overset{O}{\underset{}{C}}- \text{ or } -\overset{R''}{\underset{}{N}}-$$

each A' is independently a divalent hydrocarbyl group having from 1 to about 10, preferably from about 1 to about 4, carbon atoms; each R is independently $$-OH, -C=O,$$
$$\quad\quad\quad R'$$

or a hydroxyl substituted hydrocarbyl or a hydroxyl substituted hydrocarbyloxy group having from 1 to about 20, preferably from 1 to about 10 carbon atoms; each R' is independently hydrogen, hydroxyl or a hydrocarbyl or hydrocarbyloxy group having from 1 to about 10, preferably from 1 to about 6, carbon atoms; each R" is independently hydrogen or a hydrocarbyl group having from 1 to about 10, preferably from 1 to about 6, carbon atoms; each X is independently a hydroxyl group, a nitro group, a nitrile group, a hydrocarbyl group, a hydrocarbyloxy group, a hydroxyl substituted hydrocarbyl or a hydroxyl substituted hydrocarbyloxy group each such groups having from 1 to about 20, preferably from 1 to about 12, carbon atoms or a halogen; m has an average value of from about 0.01 to about 6, preferably from about 1 to about 3; each n independently has a value of zero or 1; each x independently has a value of from zero to 2; each y independently has a value of from zero to 4, preferably from 1 to 2 and z has a value of from zero to 3, preferably from 1 to 2; and wherein components (A) and (B) are employed in quantities which provide a molar ratio of B:A of from about 0.1:1 to about 10:1, preferably from about 1:1 to about 4:1, most preferably from about 1:1 to about 2:1.

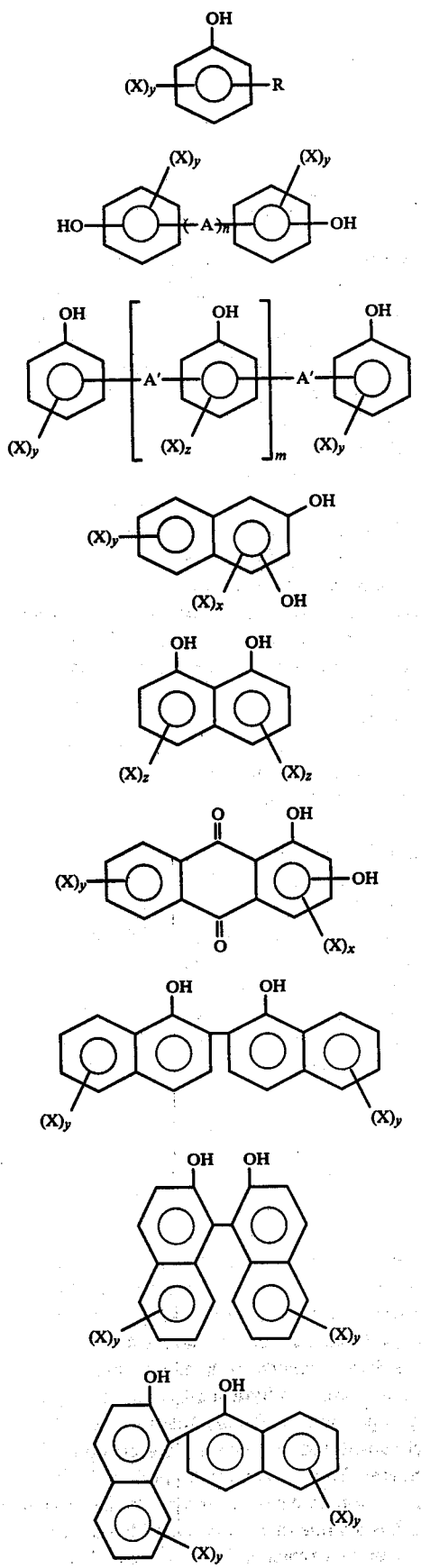

Also, another aspect of the present invention concerns a catalyst composition resulting from reacting in an inert hydrocarbon medium (A) at least one hydrocarbon soluble organomagnesium component represented by the formula $MgR''_2 \cdot xMR''_y$ wherein each $R''$ is independently a hydrocarbyl group having from 1 to 20 carbon atoms; M is a metal selected from Al, Zn, Si, Sn, B and P; y has a number corresponding to the valence of M and x has a value from about 0.001 to about 10;

(B) a halide source selected from (1) an active non-metallic halide, said non-metallic halide corresponding to the formula $R'X$ wherein $R'$ is hydrogen or a hydrocarbyl group having from 1 to about 20; preferably from 1 to about 10 carbon atoms and such that the hydrocarbyl halide is at least as active as sec-butyl chloride and does not poison the catalyst and X is halogen; or (2) a metallic halide corresponding to the formula $MR_{y-a}X_a$ wherein M is a metal of Group IIIA or IVA of Mendeleev's Periodic Table of Elements, R is a monovalent hydrocarbyl group having from 1 to about 20, preferably from 1 to about 10 carbon atoms, X is halogen, y is a number corresponding to the valence of M and a is a number from 1 to y;

(C) at least one titanium compound represented by the formula $Ti(OR)_xX_{4-x}$ wherein each R is independently a hydrocarbyl group having from 1 to about 20, preferably from about 1 to about 10, most preferably from 2 to about 4, carbon atoms; X is a halogen and x has a value from zero to 4;

(D) at least one compound containing at least one aromatic hydroxyl group represented by the formulas I, II, III, IV, V, VI, VII, VIII or IX;

wherein each A is independently a divalent hydrocarbyl group having from 1 to about 10, preferably from 1 to about 4, carbon atoms,

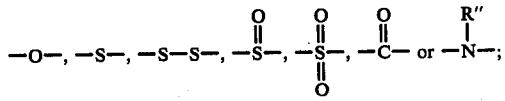

each A' is independently a divalent hydrocarbyl group having from 1 to about 10, preferably from about 1 to about 4, carbon atoms; each R is independently

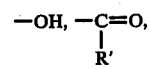

or a hydroxyl substituted hydrocarbyl or a hydroxyl substituted hydrocarbyloxy group having from 1 to about 20, preferably from 1 to about 10 carbon atoms; each $R'$ is independently hydrogen, hydroxyl or a hydrocarbyl or hydrocarbyloxy group having from 1 to about 10, preferably from 1 to about 6, carbon atoms; each $R''$ is independently hydrogen or a hydrocarbyl group having from 1 to about 10, preferably from 1 to about 6, carbon atoms; each X is independently a hydroxyl group, a nitro group, a nitrile group, a hydrocarbyl group, a hydrocarbyloxy group, a hydroxyl substituted hydrocarbyl or a hydroxyl substituted hydrocarbyloxy group each such groups having from 1 to about 20, preferably from 1 to about 12, carbon atoms or a halogen; m has an average value of from about 0.01 to about 6, preferably from about 1 to about 3; each n independently has a value of zero or 1; each x independently has a value of from zero to 2; each y independently has a value of from zero to 4, preferably from 1 to 2 and z has a value of from zero to 3, preferably from 1 to 2.

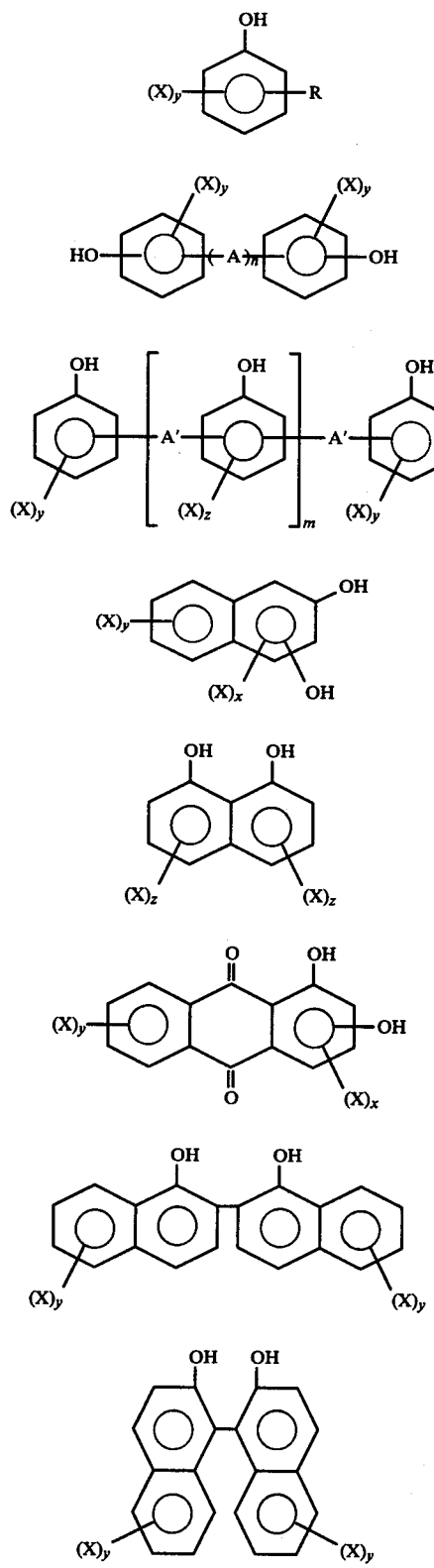

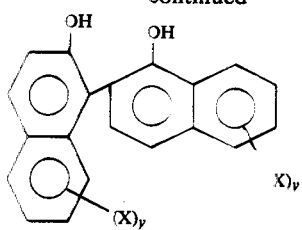

and when components (A) and/or (B) do not contain or contain an insufficient quantity of aluminum, then (E) an aluminum compound represented by the formula $AlR_{y'}X_{y''}$ wherein R is a hydrocarbyl group having from 1 to about 10, preferably from 1 to about 4, carbon atoms; X is halogen and $y'$ and $y''$ each have a value of from zero to three with the sum of $y'$ and $y''$ being three is employed;

and wherein the components are employed in quantities so as to provide the following ratios:

(1) a Mg:Ti atomic ratio of from about 1:1 to about 200:1, preferably from about 2:1 to about 100:1, most preferably from about 5:1 to about 50:1;

(2) components (D) and (C) are employed in quantities which provide a molar ratio of D:C of from about 0.1:1 to about 10:1, preferably from about 1:1 to about 4:1, most preferably from about 1:1 to about 2:1;

(3) excess X:Al ratio of from about 0.0005:1 to about 10:1, preferably from about 0.002:1 to about 2:1, most preferably from about 0.01:1 to about 1.4:1; and (4) an Al:Ti atomic ratio of from about 0.1:1 to about 2000:1, preferably from about 0.5:1 to about 200:1, most preferably from about 1:1 to about 75:1;

The excess X is the quantity of halide above that which would be theoretically required to convert the magnesium compound to the dihalide.

Still another aspect of the present invention pertains to bidentate ligand-containing titanium compounds represented by the formulas

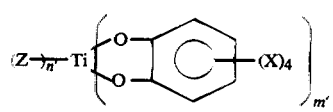

wherein each Z is independently a halogen or an $R^2O$-group; each $R^2$ is independently a hydrocarbyl group having from 1 to about 20, preferably from 1 to about 10, most preferably from 2 to about 4 carbon atoms; each X is independently a hydroxyl group, a nitro group, a nitrile group, a hydrocarbyl group, a hydrocarbyloxy group, a hydroxyl substituted hydrocarbyl or a hydroxyl substituted hydrocarbyloxy group each such groups having from 1 to about 20, preferably from 1 to about 12, carbon atoms or a halogen; $m'$ has a value of 1 or 2; $n'$ has a value of zero when $m'$ has a value of 2; $n'$ has a value of 2 when $m'$ has a value of 1; and y has a value of from zero to 4.

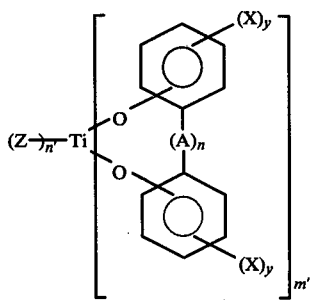

XI.

wherein each A is independently a divalent hydrocarbyl group having from 1 to about 10, preferably from 1 to about 4, carbon atoms,

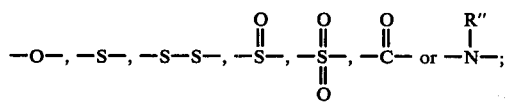

each R″ is independently hydrogen or a hydrocarbyl group having from 1 to about 10, preferably from 1 to about 6, carbon atoms; each Z is independently a halogen or an $R^2O$—group; each $R^2$ is independently a hydrocarbyl group having from 1 to about 20, preferably from about 1 to about 10, most preferably from 2 to about 4, carbon atoms; each X is independently a hydroxyl group, a nitro group, a nitrile group, a hydrocarbyl group, a hydrocarbyloxy group, a hydroxyl substituted hydrocarbyl or a hydroxyl substituted hydrocarbyloxy group each such groups having from 1 to about 20, preferably from 1 to about 12, carbon atoms or a halogen; n has a value of zero or 1; m' has a value of 1 or 2; n' has a value of zero when m' has a value of 2 and a value of 2 when m' has a value of 1; and y has a value from zero to 4.

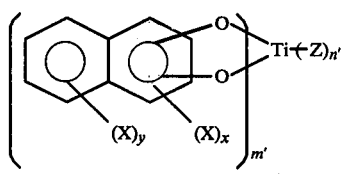

XII.

wherein Z, $R^2$, X, m', n', and y are as defined above; and x has a value from zero to 2.

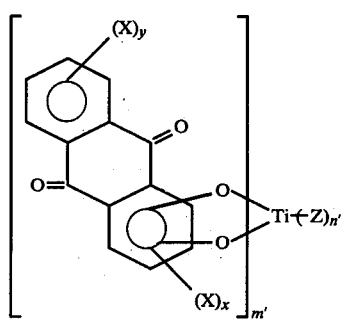

XIII.

wherein each Z, $R^2$, X, m', n', y and x are as defined above; and

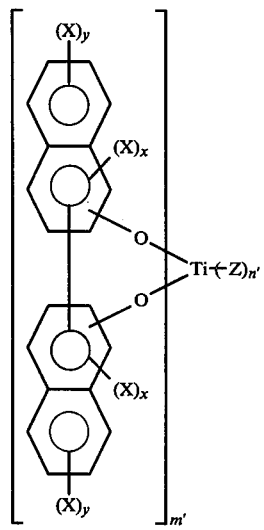

XIV.

wherein each Z, $R^2$, X, m', n', x and y are as defined above.

DESCRIPTION OF THE PREFERRED EMBODIMENTS

Suitable compounds containing at least one phenolic hydroxyl group which can be employed herein includes, for example, catechol, resorcinol, bisphenol A, 4-t-butylcatechol, bis(hydroxyphenyl)methane, 4-t-octylcatechol, 3-isopropylcatechol, 3-isopropyl-6-methylcatechol, 3,5-di-t-butylcatechol, 3-methoxycatechol, o,o'-bisphenol, alizarin, 2,3-dihydroxy naphthalene, salicylaldehyde, o-hydroxy acetophenone, o-hydroxy benzophenone, 3,4-dihydroxy benzaldehyde, 1,1'-bi-2-naphthol, 3-methoxy salicylaldehyde, mixtures thereof and the like.

Particularly suitable titanium compounds which can be employed herein include for example, tetraethoxy titanium, tetraisopropoxy titanium, tetra-n-butoxy titanium, tetraphenoxy titanium, tetra-n-propoxy titanium, tetra-(2-ethylhexoxy) titanium, di-n-butoxy titanium dichloride, titanium tetrachloride, mixtures thereof and the like.

Particularly suitable organomagnesium compounds include, for example, hydrocarbon soluble dihydrocarbylmagnesium such as the magnesium dialkyls and the magnesium diaryls. Exemplary suitable magnesium dialkyls include particularly n-butyl-sec-butyl magnesium, diisopropyl magnesium, di-n-hexyl magnesium, isopropyl-n-butyl magnesium, ethyl-n-hexyl magnesium, ethyl-n-butyl magnesium, di-n-octyl magnesium and others wherein the alkyl has from 1 to 20 carbon atoms. Exemplary suitable magnesium diaryls include diphenylmagnesium, dibenzylmagnesium, and ditolylmagnesium. Suitable organomagnesium compounds include alkyl and aryl magnesium alkoxides and aryloxides and aryl and alkyl magnesium halides with the halogen-free organomagnesium compounds being more desirable.

Among the halide sources which can be employed herein are the active non-metallic halides and metallic halides.

Suitable non-metallic halides are represented by the formula R'X wherein R' is hydrogen or an active monovalent organic radical and X is a halogen. Particularly suitable non-metallic halides include, for example, hydrogen halides and active organic halides such as t-alkyl halides, allyl halides, benzyl halides and other active hydrocarbyl halides wherein hydrocarbyl is as defined hereinbefore. By an active organic halide is meant a hydrocarbyl halide that contains a labile halogen at least as active, i.e., as easily lost to another compound, as the halogen of sec-butyl chloride, preferably as active as t-butyl chloride. In addition to the organic monohalides, it is understood that organic dihalides, trihalides and other polyhalides that are active as defined hereinbefore are also suitably employed. Examples of preferred active non-metallic halides include hydrogen chloride, hydrogen bromide, t-butyl chloride, t-amyl bromide, allyl chloride, benzyl chloride, crotyl chloride, methylvinyl carbinyl chloride, α-phenylethyl bromide, diphenyl methyl chloride and the like. Most preferred are hydrogen chloride, t-butyl chloride, allyl chloride and benzyl chloride.

Suitable metallic halides which can be employed herein include those represented by the formula $MR_{y-a}X_a$ wherein M is a metal of Groups IIB, IIIA or IVA, of Mendeleev's Periodic Table of Elements, R is a monovalent organic radical, X is a halogen, Y has a value corresponding to the valence of M and a has a value from 1 to y. Preferred metallic halides are aluminum halides of the formula $AlR_{3-a}X_a$ wherein each R is independently hydrocarbyl as hereinbefore defined such as alkyl, X is a halogen and a is a number from 1 to 3. Most preferred are alkylaluminum halides such as ethylaluminum sesquichloride, diethylaluminum chloride, ethylaluminum dichloride, and diethylaluminum bromide, with ethylaluminum dichloride being especially preferred. Alternatively, a metal halide such as aluminum trichloride or a combination of aluminum trichloride with an alkyl aluminum halide or a trialkyl aluminum compound may be suitable employed.

It is understood that the organic moieties of the aforementioned organomagnesium, e.g., R", and the organic moieties of the halide source, e.g., R and R', are suitably any other organic radical provided that they do not contain functional groups that poison conventional Ziegler catalysts.

The magnesium halide can be preformed from the organomagnesium compound and the halide source or it can be formed insitu in which instance the catalyst is preferably prepared by mixing in a suitable solvent or reaction medium (1) the organomagnesium component and (2) the halide source, followed by the other catalyst components.

The compound or complex formed from reacting said titanium component and said component having at least one aromatic hydroxyl group per molecule can be utilized as formed or the product can be isolated and then utilized at the appropriate place in the catalyst preparation.

When it is desired to prepare complexes employing molar ratios of titanium compound to hydroxyl-containing compound of about 1 to 1, it is preferred to add the hydroxyl-containing compound to the titanium compound.

When it is desired to prepare complexes employing molar ratios of titanium compound to hydroxyl-containing compound of about 1 to 2, it is preferred to add the titanium compound to the hydroxyl-containing compound.

Regardless of the molar ratios employed, when it is desired to prepare a complex containing mixed ligands by employing different hydroxyl-containing compounds, it is preferred to add the hydroxyl-containing compounds to the titanium compound wherein the most acidic hydroxyl-containing compound is added first.

When the titanium compound and aromatic hydroxyl-containing compounds are prereacted, temperatures from about 0° C. to about 200° C., preferably from about 20° C. to about 100° C., can be employed.

The foregoing catalyst components are combined in proportions sufficient to provide atomic ratios as previously mentioned.

In cases wherein neither the organomagnesium component nor the halide source contains aluminum or contains an insufficient quantity of aluminum, it is necessary to include in the total catalyst an aluminum compound such as an alkyl aluminum compound, e.g., a trialkyl aluminum, an alkyl aluminum halide or an aluminum halide. If polymerization temperatures below 180° C. are employed, the atomic ratios of Al:Ti may be from about 0.1:1 to about 2000:1, preferably from 1:1 to about 200:1. However, when polymerization temperatures above 180° C. are employed, the aluminum compound is used in proportions such that the Al:Ti ratio is less than 120:1, preferably less than 50:1. It is understood, however, that the use of very low amounts of aluminum necessitates the use of high purity solvents or diluents in the polymerization zone. Further, other components present in the zone should be essentially free of impurities which react with aluminum alkyls. Otherwise, additional quantities of an organometallic compound as previously described, preferably an organoaluminum compound, must be used to react with such impurities. Moreover, it is understood that in the catalyst the aluminum compound should be in the form of trialkyl aluminum or alkyl aluminum halide provided that the alkyl aluminum halide be substantially free of alkyl aluminum dihalide. In the above mentioned aluminum compounds, the alkyl groups independently have from 1 to about 20, preferably from 1 to about 10 carbon atoms.

When additional quantities of aluminum compound are employed, it can be added to the aforementioned catalyst during the preparation thereof or the aluminum deficient catalyst can be mixed with the appropriate aluminum compound prior to entry into the polymerization reactor or, alternatively, the aluminum deficient catalyst and the aluminum compound can be added to the polymerization reactor as separate streams or additions.

The foregoing catalytic reaction is preferably carried out in the presence of an inert diluent. The concentrations of catalyst components are preferably such that when the essential components of the catalytic reaction product are combined, the resultant slurry is from about 0.005 to about 1.0 molar (moles/liter) with respect to magnesium. By way of an example of suitable inert organic diluents can be mentioned liquified ethane, propane, isobutane, n-butane, n-hexane, the various isomeric hexanes, isooctane, paraffinic mixtures of alkanes having from 8 to 12 carbon atoms, cyclohexane, methylcyclopentane, dimethylcyclohexane, dodecane, industrial solvents composed of saturated or aromatic hydrocarbons such as kerosene, naphthas, etc., especially when free of any olefin compounds and other impurities, and especially those having boiling points in the range from about −50° to about 200° C. Also included as suitable inert diluents are benzene, toluene, ethylbenzene, cumene, decalin and the like.

Mixing of the catalyst components to provide the desired catalytic reaction product is advantageously carried out under an inert atmosphere such as nitrogen, argon or other inert gas at temperatures in the range from about −100° to about 200° C., preferably from about 0° to about 100° C. The period of mixing is not considered to be critical as it is found that a sufficient catalyst composition most often occurs within about 1 minute or less. In the preparation of the catalytic reaction product, it is not necessary to separate hydrocarbon soluble components from hydrocarbon insoluble components of the reaction product.

While the catalysts can be prepared by adding the components in essentially any order, it is preferred to add the components in one of the following orders:
 (1) A, B, (C and D, prereacted), E (if required)
 (2) A, B, E (if required), (C and D, prereacted)
 (3) (A and B, prereacted), (C and D, prereacted), E (if required)
 (4) (A and B, prereacted), E (if required), (C and D, prereacted)
 (5) (A, B and E, if required, prereacted), (C and D, prereacted)

In the polymerization process employing the aforementioned catalytic reaction product, polymerization is effected by adding a catalytic amount of the above catalyst composition to a polymerization zone containing α-olefin monomer, or vice versa. Any polymerization method can be employed including slurry, solution, gas phase, high pressure process, and the like. The polymerization zone is usually maintained at temperatures in the range from about 0° to about 300° C., preferably at solution polymerization temperatures, e.g., from about 130° to about 250° C., for a residence time of about a few seconds to several days, preferably 15 seconds to 2 hours (7200 s). It is generally desirable to carry out the polymerization in the absence of moisture and oxygen and a catalytic amount of the catalytic reaction product is generally within the range from about 0.0001 to about 0.1 millimoles titanium per liter of diluent. It is understood, however, that the most advantageous catalyst concentration will depend upon polymerization conditions such as temperature, pressure, solvent and presence of catalyst poisons and that the foregoing range is given to obtain maximum catalyst yields in weight of polymer per unit weight of titanium. Generally, in the polymerization process, a carrier which may be an inert organic diluent or solvent or excess monomer is employed. In order to realize the full benefit of the high efficiency catalyst of the present invention, care must be taken to avoid oversaturation of the solvent with polymer. If such saturation occurs before the catalyst becomes depleted, the full efficiency of the catalyst is not realized. For best results, it is preferred that the amount of polymer in the carrier not exceed about 50 weight percent based on the total weight of the reaction mixture.

It is understood that inert diluents employed in the polymerization recipe are suitable as defined hereinbefore.

The polymerization pressures preferably employed are relatively low, e.g., from about 5 to about 10,000 psig (0.034–68.9 MPa), preferably from about 50 to about 1000 psig, (0.345–6.89 MPa), most preferably from about 100 to about 700 psig (0.689–4.8 MPa). However, polymerization within the scope of the present invention can occur at pressures from atmospheric up to pressures determined by the capabilities of the polymerization equipment, which can include pressures up to about 50,000 psig (344.5 MPa). During polymerization it is desirable to stir the polymerization recipe to obtain better temperature control and to maintain uniform polymerization mixtures throughout the polymerization zone.

In order to optimize catalyst yields in the polymerization of ethylene under solution conditions, it is preferable to maintain an ethylene concentration in the solvent in the range of from about 1 to about 10 weight percent, most advantageously from about 1.2 to about 2 weight percent. To achieve this, when an excess of ethylene is fed into the system, a portion of the ethylene can be vented. In other processes, it is preferred to conduct the polymerization in an excess of the α-olefin being polymerized in order to optimize catalyst yields.

Hydrogen can be employed in the practice of this invention to control the molecular weight of the resultant polymer. For the purpose of this invention, it is beneficial to employ hydrogen in concentrations ranging from about 0.001 to about 1 mole per mole of monomer. The larger amounts of hydrogen within this range are found to produce generally lower molecular weight polymers. It is understood that hydrogen can be added with a monomer stream to the polymerization vessel or separately added to the vessel before, during or after addition of the monomer to the polymerization vessel, but during or before the addition of the catalyst.

The monomer or mixture of monomers is contacted with the catalytic reaction product in any conventional manner, preferably by bringing the catalytic reaction product and monomer together with intimate agitation provided by suitable stirring or other means. Agitation can be continued during polymerization, or in some instances, the polymerization can be allowed to remain unstirred while the polymerization takes place. In the case of more rapid reactions with more active catalysts, means can be provided for refluxing monomer and solvent, if any of the latter is present, in order to remove the heat of reaction. In any event, adequate means should be provided for dissipating the exothermic heat of polymerization. If desired, the monomer can be brought in the vapor phase into contact with the catalytic reaction product, in the presence or absence of liquid material. The polymerization can be effected in the batch manner, or in a continuous manner, such as, for example, by passing the reaction mixture through an elongated reaction tube which is contacted externally with suitable cooling media to maintain the desired reaction temperature, or by passing the reaction mixture through an equilibrium overflow reactor or a series of the same.

The polymer is readily recovered from the polymerization mixture by driving off unreacted monomer and solvent if any is employed. No further removal of impurities is required. Thus, a significant advantage of the present invention is the elimination of the catalyst residue removal steps. In some instances, however, it may be desirable to add a small amount of a catalyst deactivating reagent of the types conventionally employed for deactivating Ziegler catalysts. The resultant polymer is found to contain insignificant amounts of catalyst residue and to possess a relatively narrow molecular weight distribution.

The following examples are given to illustrate the invention, and should not be construed as limiting its scope. All percentages are by weight and all parts are by molar or atomic ratio unless otherwise indicated.

In the following examples, the melt index values $I_2$ and $I_{10}$ were determined by ASTM D 1238-70 and the density values were determined by ASTM D 1248.

EXAMPLES

The position of ring substituents employed herein are in accordance with the Definitive Rules for Nomenclature of Organic Chemistry as provided in the *Handbook of Chemistry and Physics*, 50th Ed., Chemical Rubber Co., page C-1 et seq.

Preparation of Complexes

The new titanium complexes were prepared by mixing stock solutions (0.015 molar) of the titanium source, titanium tetrachloride (TiCl$_4$) or titanium tetraisopropoxide (tipt), and the aromatic hydroxyl ligand in the desired ratio. The ratio (L/M) of moles ligand (L) to moles of titanium in the titanium source (M) utilized to prepare the desired complexes employed in the following examples is shown under the column heading L/M. The various stock solutions were prepared at ambient temperatures by diluting the titanium source and/or ligand with Isopar ® E (an isoparaffinic hydrocarbon fraction having a boiling range of 116°-134° C.) to the desired volume to produce 0.015 molar solutions. These stock solutions were stored under a nitrogen atmosphere to prevent decomposition.

Complexes were prepared by mixing at ambient conditions (~25° C.) 1.0 or 2.0 cc of the 0.015 m stock titanium source with the required amount of stock ligand (0.015 m) solution to give the desired molar ligand to metal ratio (L/M). The mixture, usually colored, was allowed to sit for at least 5 minutes after which time it was added to the catalyst make up in place of the normal titanium source.

Preparation of Catalyst Compositions

Method A

The catalyst compositions were prepared by adding with stirring under a nitrogen atmosphere to a 4-ounce (118.3 cc) serum bottle the following components in the indicated order.

| | |
|---|---|
| 91 − x cc | of Isopar ® E |
| 4.0 cc | of 0.15 m di-butyl magnesium* |
| 5.0 cc | of 0.15 m ethyl aluminum dichloride (EADC) |
| x cc | of titanium source or novel complex |
| 100.0 cc | total |

*Dibutylmagnesium is a commercial product of the Lithium Corporation of America. Its composition is indicated to be predominately n-butyl-s-butyl magnesium. Other commercially available magnesium alkyls that can be utilized are manufactured by Texas Alkyls and marketed under the tradename Bomag.

All final catalyst solutions were 0.00015 molar in titanium and the volume of catalyst normally injected for a polymerization run was 10 cc (0.0015 mmoles Ti). The atomic ratio of Mg/Al/Cl/Ti for these catalysts were 40/50/100/1.

Method B

1. Preparation of Anhydrous MgCl$_2$

To 21.16 ml of 0.709 molar dibutyl magnesium was added 78.84 ml of Isopar ® E. Anhydrous electronic grade HCl was passed through the solution until all of the magnesium alkyl had been converted to magnesium chloride. Excess HCl was stripped from the slurry by purging with dry N$_2$. The resulting slurry (0.15 molar) of MgCl$_2$ in Isopar ® E was stored under a nitrogen atmosphere and utilized as a stock solution in the preparation of catalyst compositions.

2. Catalyst Compositions

The catalyst compositions were prepared by adding with stirring under a nitrogen atmosphere to a 4-ounce (118.3 cc) serum bottle the following components in the indicated order.

| | |
|---|---|
| 88 − x cc | of Isopar ® E |
| 8.0 cc | of 0.15 m MgCl$_2$ (as prepared above) |
| 2.0 cc | of 0.15 m diethyl aluminum chloride (DEAC) as excess halide source |
| x cc | of titanium source or novel complex |
| 2.0 cc | of 0.15 m triethyl aluminum (TEA) |
| 100.0 cc | total |

All final catalyst solutions were 0.0003 molar in titanium and the volume of catalyst normally injected for a polymerization run was 15 cc (0.0045 millimoles Ti). The atomic ratios of Mg/Al/Cl/Ti for these catalysts were 40/20/90/1.

3. Catalyst Compositions

The catalyst compositions were prepared by adding with stirring under a nitrogen atmosphere to a 4-ounce (118.3 cc) serum bottle the following components in the indicated order.

| | |
|---|---|
| 100 − (A + B + (x or y) + z cc of Isopar ® E | |
| B cc of 0.15 MgCl$_2$ | |
| x cc of 0.15 DEAC (or) | as excess halide source |
| y cc of 0.15 EADC | |
| z cc of titanium source or novel complex | |
| A cc of 0.15 m TEA | |
| 100.0 cc total | |

All final catalyst solutions were 0.0003 molar in titanium and the volume of catalyst normally injected for a polymerization run was 15 cc (0.0045 millimoles). The final atomic ratios of Mg/Al/Cl/Ti are shown in the appropriate Tables.

POLYMERIZATION CONDITIONS

General Procedure

A stirred, 1 gallon (3.79 l) batch reactor containing 2 liters of Isopar ® E was heated to the desired temperature and the solvent vapor pressure recorded. To this was added 5-6 psig (34-41 kPa) of hydrogen and the ethylene was added to give the desired final reactor pressure. An amount of the above catalyst was injected into the reactor and the reactor pressure was maintained constant at the desired final pressure by continually feeding ethylene during the polymerization run. The total reaction time was 20 minutes (1200 s). The novel titanium species, the L/M ratio utilized in its preparation and the resulting catalyst efficiencies are given in the following tables. All catalyst efficiencies are given as grams of polyethylene produced per gram of titanium employed in the 20 minutes (1200 s) polymerization run.

| Con- dition | Temper- ature °C. | Polymerization Conditions | | | Final Total Pressure psig/kPa |
|---|---|---|---|---|---|
| | | Solvent Vapor Pressure psig/kPa | Hydrogen Added psig/kPa | Ethylene Added psig/kPa | |
| A | 150 | 21/145 | 6/41 | 173/1193 | 200/1379 |
| B | 180 | 50/345 | 5/35 | 145/1000 | 200/1379 |
| C | 195 | 60/414 | 5/35 | 385/2655 | 450/3103 |
| D | 210 | 70/483 | 5/35 | 375/2586 | 450/3103 |
| E | 190 | 55/379 | 5/35 | 290/2000 | 350/2413 |
| F | 190 | 55/379 | 5/35 | 345/2379 | 400/2758 | wherein X and R' are identified in the table, and y has a value of 1. The number accompanying the identifying group represents the location which the inventors herein believe the X group is positioned on the ring.

The data in Table I demonstrates that catalysts employing the complexes of the present invention have higher catalyst efficiencies based upon titanium than when a different titanium source is employed.

Table II provides results obtained when the titanium compound is tetraisopropyltitanate and the hydroxyl-containing compound is represented by the formula

TABLE I

| Example[1] or Comparative Experiments[2] | Polymeri- zation Method | Catalyst Preparation Method | X | R' | L/M | Ti EFF. $\times 10^{-6}$ | $I_2$ | $I_{10}$ | $I_{10}/I_2$ | Exotherm °C. |
|---|---|---|---|---|---|---|---|---|---|---|
| 1 | A | A | H | H | 1/1 | 1.93 | 9.49 | 69.63 | 7.34 | 19 |
| 2 | " | " | " | " | 2/1 | 2.01 | 9.89 | 74.18 | 7.50 | 19 |
| 3 | A | A | 5-CH$_3$O | H | 1/1 | 1.97 | 9.58 | 72.07 | 7.52 | 18 |
| 4 | " | " | " | " | 2/1 | 1.99 | 9.02 | 65.63 | 7.28 | 17 |
| 5 | A | A | H | —CH$_3$ | 1/1 | 2.02 | 10.38 | 75.02 | 7.22 | 20 |
| 6 | " | " | " | " | 2/1 | 1.93 | 8.95 | 65.20 | 7.28 | 20 |
| 7 | A | A | 5-CH$_3$ | —CH$_3$ | 1/1 | 1.98 | 9.74 | 71.39 | 7.33 | 19 |
| 8 | " | " | " | " | 2/1 | 1.98 | 7.49 | 61.10 | 8.16 | 18 |
| A[3] | A | A | — | — | — | 1.90 | 10.4 | 76.14 | 7.32 | 17 |

FOOTNOTES TO TABLE I
[1]Examples of the present invention are indicated by numbers.
[2]Comparative Experiments are indicated by letters.
[3]No hydroxyl-containing compound was employed. The titanium source was tetraisopropyl titanate.

Table I provides the results obtained when the titanium compound is tetraisopropyltitanate and a hydroxyl-containing compound represented by the formula

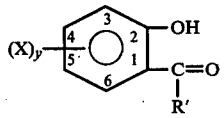

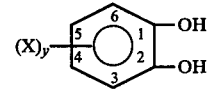

wherein X is identified in the table, and y has a value of zero to 2. The number accompanying the identifying group corresponds to the location which the inventors herein believe the X group(s) is/are positioned on the ring.

TABLE II

| Example[1] or Comparative Experiment[2] | Polymeri- zation Method | Catalyst Prepara- tion Method | X | L/M | Ti EFF. $\times 10^{-6}$ | $I_2$ | $I_{10}$ | $I_{10}/I_2$ | Exo- therm °C. |
|---|---|---|---|---|---|---|---|---|---|
| 13 | A | A | H | 1/1 | 2.003 | 10.62 | 78.31 | 7.37 | 19 |
| 14 | A | A | H | 2/1 | 2.101 | 15.70 | 109.87 | 6.99 | 19 |
| 15 | A | A | 4-CH$_3$ | 1/1 | 2.216 | 12.27 | 85.68 | 6.98 | 15 |
| 16 | A | A | 4-CH$_3$ | 2/1 | 2.279 | 10.79 | 75.52 | 7.0 | 17 |
| 17 | A | A | 4-t-butyl | 1/1 | 2.288 | 16.42 | 107.67 | 6.56 | 20 |
| 18 | A | A | 4-t-butyl | 2/1 | 2.432 | 16.89 | 116.92 | 6.92 | 18 |
| 19 | A | A | 3,5-di-t- butyl | 1/1 | 2.323 | 11.37 | 127.10 | 11.18 | 20 |
| 20 | A | A | 3,5-di-t- butyl | 2/1 | 2.225 | 16.18 | 110.64 | 6.84 | 15 |
| 21 | A | A | NAP[4] | 1/1 | 2.684 | 16.10 | 114.48 | 7.11 | 18 |
| 22 | A | A | NAP[4] | 2/1 | 2.787 | 20.22 | 140.28 | 6.94 | 22 |
| B[3] | A | — | — | — | 1.75 | 9.30 | 72.62 | 7.81 | 20 |
| 23 | B | B-2 | H | 1/1 | .541 | 13.38 | 96.48 | 7.21 | 15 |
| 24 | B | B-2 | H | 2/1 | .570 | 26.94 | 189.96 | 7.05 | 18 |
| 25 | B | B-2 | 4-CH$_3$ | 1/1 | .525 | 21.02 | 175.44 | 8.35 | 17 |
| 26 | B | B-2 | 4-CH$_3$ | 2/1 | .605 | 25.3 | 180.25 | 7.12 | 18 |
| 27 | B | B-2 | 4-t-butyl | 1/1 | .546 | 18.08 | 158.13 | 8.75 | 17 |
| 28 | B | B-2 | 4-t-butyl | 2/1 | .614 | 26.5 | 182.79 | 6.90 | 21 |
| 29 | B | B-2 | 3,5-di-t- butyl | 1/1 | .557 | 28.7 | 213.24 | 7.43 | 17 |
| 30 | B | B-2 | 3,5-di-t- butyl | 2/1 | .573 | 25.32 | 171.84 | 6.79 | 15 |

| Example[1] or Comparative Experiment[2] | Polymerization Method | Catalyst Preparation Method | Z | L/M | Ti EFF. × 10^-6 | $I_2$ | $I_{10}$ | $I_{10}/I_2$ | Exotherm °C. |
|---|---|---|---|---|---|---|---|---|---|
| 31 | B | B-2 | NAP[4] | 1/1 | 0.540 | 23.12 | 142.5 | 6.16 | 20 |
| 32 | B | B-2 | NAP[4] | 2/1 | 0.589 | 28.48 | 188.88 | 6.63 | 19 |
| C[3] | B | B-2 | — | — | 0.419 | 21.57 | 117.60 | 5.45 | 14 |
| 33 | C | B-2 | H | 1/1 | .901 | 17.98 | 129.66 | 7.21 | 18 |
| 34 | C | B-2 | H | 2/1 | .934 | 16.90 | 126.69 | 7.50 | 21 |
| 35 | C | B-2 | 4-t-butyl | 1/1 | 0.922 | 15.53 | 117.27 | 7.55 | 19 |
| 36 | C | B-2 | 4-t-butyl | 2/1 | 1.05 | 21.51 | 150.17 | 6.98 | 18 |
| D[3] | C | B-2 | — | — | 0.55 | 13.41 | 103.86 | 7.74 | 11 |
| 37 | D | B-2 | 4-t-butyl | 1/1 | 0.533 | 23.30 | 169.68 | 7.28 | 10 |
| 38 | D | B-2 | 4-t-butyl | 2/1 | 0.600 | 36.56 | 250.24 | 6.84 | 12 |
| E[3] | D | B-2 | — | — | 0.355 | N.D.[6] | N.D.[6] | N.D.[6] | 7 |
| 39[5] | C | B-2 | H | 1/1 | 0.489 | 8.86 | 66.7 | 7.53 | 10 |
| 40[5] | C | B-2 | H | 2/1 | 0.532 | 11.09 | 88.71 | 8.00 | 12 |
| 41[5] | C | B-2 | 4-t-butyl | 1/1 | 0.701 | 9.04 | 96.48 | 10.67 | 14 |
| 42[5] | C | B-2 | 4-t-butyl | 2/1 | 0.793 | 12.7 | 171.61 | 13.51 | 17 |
| F[3,5] | C | B-2 | — | — | 0.298 | 6.28 | 74.59 | 11.88 | 7 |

FOOTNOTES TO TABLE II
[1]Examples of the present invention are represented by numbers. Example numbers 9 through 12 were intentionally omitted.
[2]Comparative Experiments are represented by letters.
[3]No hydroxyl-containing compound was employed. The titanium source was tetraisopropyl titanate.
[4]NAP = 2,3-dihydroxynaphthalene.
[5]Titanium tetrachloride was employed instead of tetraisopropyltitanate. The Mg/Al/Cl/Ti atomic ratio was 40/20/94/1.
[6]N.D. means the property was not determined.

The data in Table II demonstrates that the novel titanium complexes provide an improvement in catalyst efficiency based on titanium at various methods of catalyst preparation and varying polymerization conditions.

The following Table III compares the results obtained from catalysts prepared by the sequential addition of the titanium compound and the hydroxyl-containing compound (Example 43) with the results obtained from prereacting the titanium compound with the hydroxyl-containing compound (Example 44) and no hydroxyl-containing compound (Comparative Experiment G). The polymerization conditions employed were C. The catalysts were prepared using method B-2.
EADC = ethylaluminum dichloride.
TiPT = tetraisopropyltitanate.

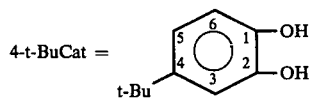

4-t-BuCat =

TEA = triethylaluminum.
The L/M ratio in Examples 43 and 44 was 2/1.

TABLE III

| Example Number | Order of Addition | Ti EFF × 10^-6 |
|---|---|---|
| G | MgCl$_2$/EADC/TiPT/TEA | 0.551 |
| 43 | MgCl$_2$/EADC/TiPT/4-t-BuCat/TEA | 0.642 |
| 44 | MgCl$_2$/EADC/(TiPT + 4-t-BuCat)/TEA | 0.698 |

Table IV provides results obtained with different titanium complexes. The formulas refer to those employed in the specification. The polymerization method employed was E. The catalyst preparation method employed was B-3. The titanium compound (M) and hydroxyl-containing compound (L) were prereacted prior to use.
TiPT = tetraisopropyltitanate
DEAC = diethylaluminum chloride
EADC = ethylaluminum dichloride.

TABLE IV

| Example | Titanium Compound | Hydroxyl-Containing Compound | Excess Halide Source | L/M Ratio | Final Catalyst Ratio Mg/Al/Cl/Ti | Excess X to Ti Ratio | Ti EFF. × 10^-6 |
|---|---|---|---|---|---|---|---|
| 45 | TiPT | Formula - I R = 2-OH, X = 3-isopropyl, y = 1 | DEAC | 2/1 | 40/24/88/1 | 3 | 1.06 |
| 46 | TiPT | Formula - I R = 2-OH, X = 3-isopropyl, y = 1 | DEAC | 2/1 | 40/30/94/1 | 4 | 1.33 |
| 47 | TiPT | Formula - I R = 2-OH, X = 3-isopropyl, y = 1 | DEAC | 2/1 | 40/36/100/1 | 10 | 1.48 |
| 48 | TiPT | Formula I, R = 2-OH, X = 3-t-butyl and 5-t-butyl, y = 2 | DEAC | 2/1 | 40/18/87.5/1 | 7.5 | 1.34 |
| 49 | TiPT | Formula I, R = 2-OH, X = 3-t-butyl and 5-t-butyl, y = 2 | DEAC | 2/1 | 40/12/87.5/1 | 7.5 | 1.02 |
| 50 | TiPT | Formula I, R = 2-OH, X = 3-t-butyl | DEAC | 2/1 | 40/24/87.5/1 | 7.5 | 1.30 |

TABLE IV-continued

| Example | Titanium Compound | Hydroxyl-Containing Compound | Excess Halide Source | L/M Ratio | Final Catalyst Ratio Mg/Al/Cl/Ti | Excess X to Ti Ratio | Ti EFF. × $10^{-6}$ |
|---|---|---|---|---|---|---|---|
| 51 | TiPT | and 5-t-butyl, y = 2 Formula I, R = 2-OH, X = 3-t-butyl and 5-t-butyl, y = 2 | DEAC | 2/1 | 40/30/92.5/1 | 12.5 | 2.19 |
| 52 | TiPT | Formula I R = 2-OH, X = 3-methoxy, y = 1 | DEAC | 2/1 | 40/30/100/1 | 20 | 0.9 |
| 53 | TiPt | Formula II, n = 0, y = 0 bridging in the o,o' position | DEAC | 2/1 | 40/14/85/1 | 5 | 1.01 |
| 54 | TiPT | Formula II, n = 0, y = 0 bridging in the o,o' position | DEAC | 2/1 | 40/10/85/1 | 5 | 1.13 |
| 55 | TiPT | Formula II, A = —CH$_2$—, n = 1, y = 0, bridging in the o,o' position | DEAC | 2/1 | 40/18/94/1 | 14 | 1.66 |
| 56 | TiPT | Formula II, A = —CH$_2$—, n = 1, y = 0, bridging in the o,o' position | DEAC | 2/1 | 40/22/94/1 | 14 | 1.85 |
| 57 | TiPT | Formula II, A = —CH$_2$—, n = 1, y = 0, bridging in the o,o' position | DEAC | 2/1 | 40/24/91/1 | 11 | 1.68 |
| 58 | TiPT | Formula II, A = —CH$_2$—, X = 3-t-butyl and 3'-t-butyl, 5-methyl and 5'-methyl, each y = 2, n = 1, bridging in the o,o' position | EADC | 2/1 | 40/30/110/1 | 30 | 1.02 |
| 59 | TiPT | Formula II, A = —CH$_2$—, X = 3-t-butyl and 3'-t-butyl, 5-methyl and 5'-methyl, each y = 2, n = 1, bridging in the o,o' position | EADC | 2/1 | 40/40/95/1 | 15 | 0.99 |

The following Table V demonstrates the results obtained using various support (MgCl$_2$)/Ti ratios. The catalyst was prepared by procedure B-3 using the following compounds and indicated mole ratios.

| varing | MgCl$_2$ |
|---|---|
| 5 | diethylaluminum chloride (excess halide source) |
| 1 | tetraisopropyltitanate ⎫ |
| 2 | 4-t-butyl-catechol ⎬ prereacted |
| 13 | triethylaluminum ⎭ |

Polymerization method F was employed.

TABLE V

| Example[1] or Comparative Experiment[2] | Mg/Ti | Exotherm °C. | $I_2$ | $I_{10}$ | $I_{10}/I_2$ | Ti Efficiency × $10^{-6}$ |
|---|---|---|---|---|---|---|
| 60 | 5 | 5 | 1.65 | 12.7 | 7.69 | 0.692 |
| 61 | 10 | 6 | 1.92 | 16.6 | 8.65 | 0.838 |
| 62 | 20 | 6 | 2.74 | 21.64 | 7.90 | 0.971 |
| 63 | 30 | 8 | 4.52 | 32.69 | 7.23 | 1.01 |
| 64 | 40 | 7 | 4.28 | 32.11 | 7.50 | 1.09 |
| H[3] | 40 | 7 | — | — | — | 0.745 |
| I[3] | 10 | 2 | — | — | — | 0.292 |

FOOTNOTES TO TABLE V
[1]Examples of the present invention are represented by numbers.
[2]Comparative Experiments are represented by letters.
[3]No hydroxyl-containing compound was employed. The titanium source was tetraisopropyl titanate.

Table VI demonstrates the results obtained at various levels of excess halide source. The catalyst was prepared by method B-3 and the polymerization was conducted by method C. Tetraisopropyl titanium was employed as the titanium compound, 4-t-butylcatechol was employed as the hydroxyl-containing compound and ethylaluminum dichloride (EADC) or diethylaluminum chloride (DEAC) was employed as the excess halide source. The L/M ratio was 2/1.

TABLE VI

| Example[6] or Comparative Experiment[7] | Ti Eff.[1] | Mg Eff.[2] | Cl Eff.[3] | Mg | Al | Cl | Ti | Excess Cl |
|---|---|---|---|---|---|---|---|---|
| 65[4] | 86291 | 4250.1 | 1413.2 | 40 | 20 | 82.5 | 1 | 2.5 |
| 66[4] | 105080 | 5175.6 | 1577.5 | 40 | 20 | 90 | 1 | 10 |
| 67[4] | 130132 | 6409.5 | 2131.1 | 40 | 24 | 82.5 | 1 | 2.5 |
| 68[4] | 204593 | 10076.9 | 2909.7 | 40 | 20 | 95 | 1 | 15 |
| 69[4] | 254697 | 12544.7 | 3622.3 | 40 | 24 | 95 | 1 | 15 |
| 70[4] | 259569 | 12784.7 | 4125.9 | 40 | 20 | 85 | 1 | 5 |
| 71[4] | 328462 | 16177.9 | 5379.2 | 40 | 28 | 82.5 | 1 | 2.5 |
| 72[4] | 354210 | 17446.1 | 5037.6 | 40 | 32 | 95 | 1 | 15 |
| 73[4] | 375087 | 18474.3 | 5334.5 | 40 | 28 | 95 | 1 | 15 |
| 74[4] | 422408 | 20805.1 | 6341.2 | 40 | 24 | 90 | 1 | 10 |
| 75[4] | 519833 | 25603.6 | 7803.8 | 40 | 32 | 90 | 1 | 10 |
| 76[4] | 576896 | 28414.2 | 8660.4 | 40 | 28 | 90 | 1 | 10 |
| 77[4] | 594990 | 29305.3 | 9457.4 | 40 | 32 | 85 | 1 | 5 |
| 78[4] | 691719 | 34069.6 | 10994.9 | 40 | 24 | 85 | 1 | 5 |
| 79[4] | 768963 | 37874.1 | 12222.8 | 40 | 28 | 85 | 1 | 5 |
| 80[5] | 842032 | 41473.0 | 13706.7 | 40 | 14 | 83 | 1 | 3 |
| 81[5] | 869868 | 42844.0 | 14159.8 | 40 | 16 | 83 | 1 | 3 |
| 82[5] | 1155184 | 56896.9 | 18361.8 | 40 | 22 | 85 | 1 | 5 |
| 83[5] | 1155184 | 56896.9 | 18361.8 | 40 | 22 | 85 | 1 | 5 |
| 84[5] | 1176061 | 57925.1 | 18693.6 | 40 | 20 | 85 | 1 | 5 |
| 85[5] | 1176061 | 57925.1 | 18693.6 | 40 | 20 | 85 | 1 | 5 |
| 86[5] | 1183020 | 58267.9 | 17759.6 | 40 | 20 | 90 | 1 | 10 |
| 87[5] | 1183020 | 58267.9 | 17759.6 | 40 | 18 | 90 | 1 | 10 |
| 88[5] | 1183020 | 58267.9 | 16824.8 | 40 | 18 | 95 | 1 | 15 |
| 89[5] | 1183020 | 58267.9 | 19257.4 | 40 | 18 | 83 | 1 | 3 |
| 90[5] | 1189979 | 58610.6 | 18480.0 | 40 | 20 | 87 | 1 | 7 |
| 91[5] | 1210856 | 59638.9 | 18177.4 | 40 | 22 | 90 | 1 | 10 |
| 92[5] | 1217815 | 59981.6 | 17319.7 | 40 | 20 | 95 | 1 | 15 |
| 93[5] | 1224774 | 60324.4 | 19020.4 | 40 | 18 | 87 | 1 | 7 |
| 94[5] | 1252610 | 61695.4 | 19910.4 | 40 | 18 | 85 | 1 | 5 |
| 95[5] | 1252610 | 61695.4 | 17814.5 | 40 | 22 | 95 | 1 | 15 |
| J[4] | 562000 | 27680.1 | 8436.9 | 40 | 20 | 90 | 1 | 10 |
| K[5] | 603000 | 29700.0 | 9052.5 | 40 | 20 | 90 | 1 | 10 |

FOOTNOTES TO TABLE VI
[1] g PE/g Ti
[2] g PE/g Mg
[3] g PE/g Cl
[4] excess halide source was EADC
[5] excess halide source was DEAC
[6] Examples of the present invention are represented by numbers
[7] Comparative experiments are represented by letters.

Table VII discloses the results obtained employing different titanium complexes and different excess halide sources. The catalysts were prepared employing method B-3.

TABLE VII

| Example[1] or Comparative Experiment[2] | Titanium Compound | L/M Ratio | Hydroxyl-Containing Compound | Excess Halide Source | Atomic Ratios Mg/Al/Cl/Ti/excess Cl | Efficiency g PE/g Ti X10[-6] |
|---|---|---|---|---|---|---|
| 96[4] | TiPT | 2/1 | Formula I wherein R = 2-OH, y = 1 X = 4-NO$_2$ | DEAC | 40/38/104/1/24 | 0.70 |
| 97[3] | TiPT | 1/1 | Formula II wherein A = —CH$_2$—; n = 1; y = 2; X = 3,3'-di-t-butyl; and 5,5'-dimethyl; bridging is o,o' position | EADC | 40/36/108/1/28 | 0.60 |
| 98[3] | TiPT | 1/1 | Formula II wherein A = —CH$_2$—; n = 1; y = 2; X = 3,3'-di-t-butyl; and 5,5'-dimethyl; bridging is o,o' position | DEAC | 40/24/102/1/22 | 0.70 |
| 99[3] | TiPT | 2/1 | Formula II wherein A = isopropylidene; n = 1; y = 0; bridging is p,p' position | DEAC | 40/25/95/1/15 | 0.65 |
| 100[3] | TiPT | 1/1 | Formula II wherein A = isopropylidene; n = 1; y = 0; bridging is p,p' position | EADC | 40/20/90/1/10 | 0.54 |
| 101[3] | TiPT | 1/1 | Formula II wherein A = isopropylidene; n = 1; y = 0; bridging is p,p' position | DEAC | 40/20/95/1/15 | 0.52 |
| 102[3] | TiPT | 1 + 1[5]/1 | 1st Ligand Formula I wherein R = 2-OH; X = 3-OCH$_3$; y = 1 2nd Ligand Formula I | DEAC | 40/20/95/1/15 | 0.90 |

TABLE VII-continued

| Example[1] or Comparative Experiment[2] | Titanium Compound | L/M Ratio | Hydroxyl- Containing Compound | Excess Halide Source | Atomic Ratios Mg/Al/Cl/Ti/excess Cl | Efficiency g PE/g Ti X10$^{-6}$ |
|---|---|---|---|---|---|---|
| 103[3] | TiPT | 1 + 1/1 | wherein R = 2-OH; X = 4-t-butyl; y = 1 1st Ligand | DEAC | 40/20/85/1/5 | 1.02 |
|  |  |  | wherein R = 2-OH; X = 4-t-butyl; y = 1 2nd Ligand |  |  |  |
| 104[3] | TiPT | 1 + 1/1 | Formula II wherein n = 0; y = 0; bridging is o,o' position 1st Ligand | EADC | 40/20/85/1/5 | 0.979 |
|  |  |  | wherein R = 2-OH; X = 4-t-butyl; y = 1 2nd Ligand |  |  |  |
| 105[3] | TiPT | 1 + 1/1 | Formula II wherein n = 0; y = 0; bridging is o,o' position 1st Ligand | EADC | 40/25/85/1/5 | 0.970 |
|  |  |  | Formula I wherein R = 2-OH; y = 0 2nd Ligand |  |  |  |
|  |  |  | Formula I wherein R = 2-OH; X = 4-t-butyl; y = 1 |  |  |  |
| 106[3] | TiPT | 1 + 1/1 | 1st Ligand | DEAC | 40/25/85/1/5 | 1.04 |
|  |  |  | Formula I wherein R = 2-OH; y = 0 2nd Ligand |  |  |  |
|  |  |  | Formula I wherein R = 2-OH; X = 4-t-butyl; y = 1 |  |  |  |
| 107[3] | TiPT | 2/1 | Formula I wherein R = 3-OH; X = 1-formyl; y = 1 | DEAC | 40/20/90/1/10 | 0.752 |
| 108[3] | TiPT | 2/1 | Formula II wherein A = $-\overset{O}{\underset{\|}{C}}-$; y = 0; n = 1; bridging is o,o' position | DEAC | 40/18/85/1/5 | 0.843 |
| 109[3] | TiPT | 2/1 | Formula I wherein R = 3-OH; X = 1-cyano; y = 1 | DEAC | 40/18/85/1/5 | 0.388 |
| 110[4] | TiPT | 2/1 | Formula VI wherein x = 0; y = 0; the OH groups are in positions 1 and 2 | DEAC | 40/18/85/1/5 | 0.570 |
| 111[4] | TiPT | 2/1 | Formula I wherein R = 2-OH; X = 3-isopropyl and 6-methyl; y = 2 | DEAC | 40/22/94/1/14 | 2.076 |
| 112[4] | TiPT | 2/1 | Formula I wherein R = 2-OH; X = 4-t-octyl; y = 1 | DEAC | 40/18/85/1/5 | 2.839 |

FOOTNOTES TO TABLE VII
[1] Examples of the present invention are designated by numbers.
[2] Comparative experiments are designated by letters.
[3] Polymerization method C.
[4] Polymerization method E.
[5] 1 + 1 means 2 different Ligands were employed, each at an L/M ratio of 1/1.

EXAMPLES 113-114

Preparation of Catalyst from Solid Recovered Compound or Complex and Polymerization of Ethylene The following Table VIII compares the results obtained when the complex is prepared insitu and utilized as such (113) with the isolated recovered complex (114). The polymerization conditions were C. The catalysts were prepared by procedure B-3. The isolated complex of Example 114 is believed to be that represented by formula X wherein X=4-t-butyl; n'=0; m'=2; y=1.

Preparation and Recovery of Titanium Compounds or Complexes 0.01 mole of the hydroxyl-containing compound was placed in 30 ml of pentane. To this stirring pentane solution was added dropwise 0.005 mole of tetraisopropoxy titanium dissolved in 30 ml of oxygen-free pentane. Stirring was continued for 3 hours (10800 s). For t-butylcatechol, 3,5-di-t-butylcatechol, 3-isopropylcatechol, the resulting dark red solutions were evaporated to dryness on a rotary evaporator leaving a dark red solid material. For the other hydroxyl-containing materials, the complexes or compounds were isolated on a medium filter frit. All of the complexes or compounds were dried at 100° C. in a vacuum oven with a nitrogen purge overnight. All of the catechol complexes or compounds were rust red in color while the others were orange yellow. The components and results are given in the following Table IX.

TABLE VIII

| Example[1] or Comparative Experiment[2] | Titanium Compound | L/M Ratio | Hydroxyl-Containing Compound | Excess Halide Source | Atomic Ratios Mg/Al/Cl/Ti/excess Cl | Efficiency g PE/g Ti $\times 10^{-6}$ |
|---|---|---|---|---|---|---|
| L[3] | TiPT | — | None | EADC | 40/20/90/1/10 | 0.780 |
| 113 | TiPT | 2/1 | Formula I wherein R = 2-OH; X = 4-t-butyl; y = 1 | DEAC | 40/30/90/1/10 | 1.30 |
| 114 | TiPT | 2/1 | Formula I wherein R = 2-OH; X = 4-t-butyl; y = 1 | DEAC | 40/30/90/1/10 | 1.164 |

[1]Examples of the present invention are represented by numbers.
[2]Comparative experiments are represented by letters.
[3]No hydroxyl-containing compound was employed. The titanium source was tetraisopropyl titanium.

TABLE IX

| | | | Analysis | | | | The Complexes Are |
| | | | Theoretical | | Actual | | Believed To Be |
| Example No. | Hydroxyl-Containing Material | L/M Ratio | Carbon % by wt. | Hydrogen % by wt. | Carbon % by wt. | Hydrogen % by wt. | Represented By The indicated Formula |
|---|---|---|---|---|---|---|---|
| 115 | Formula I wherein R = 2-OH; X = 4-t-butyl; y = 1 | 2/1 | 62.3 | 6.5 | 61.8 | 6.7 | Formula X[1] wherein X = 4-t-butyl; y = 1; n' = 2; n' = 0 |
| 116 | Formula II wherein n = 0; y = 0; bridging is o,o' | 2/1 | 66.4 | 4.2 | 66.3 | 3.9 | Formula XI[2] wherein n = 0; y = 0; m' = 2; n' = 0 and the bridging is in the o,o' positions |
| 117 | Formula II wherein A = —CH$_2$—; n = 1; y = 2; X = 3,3'-di-t-butyl and 5,5'-dimethyl; bridging is o,o' | 2/1 | 75.3 | 8.4 | 75.5 | 8.4 | Formula XI[1] wherein A = —CH$_2$—; n = 1; X = 3,3'-di-t-butyl and 5,5'-dimethyl; bridging is o,o'; n' = 2; n' = 0; y = 2 |
| 118 | Formula IV wherein x = 0; y = 0; hydroxyl groups are in | 2/1 | 64.4 | 3.5 | 64.0 | 4.2 | Formula XII[1] wherein y = 0, x = 0, and the oxygens are in the 2,3 positions |

TABLE IX-continued

| Example No. | Hydroxyl-Containing Material | L/M Ratio | Analysis | | | | The Complexes Are Believed To Be Represented By The Indicated Formula |
|---|---|---|---|---|---|---|---|
| | | | Theoretical | | Actual | | |
| | | | Carbon % by wt. | Hydrogen % by wt. | Carbon % by wt. | Hydrogen % by wt. | |
| | the 2,3 positions | | | | | | |
| 119 | Formula VI wherein x = 0; y = 0; hydroxyl groups are in the 1,2 positions | 2/1 | 62.0 | 2.6 | 61.8 | 2.5 | Formula XIII[2], x = 0, y = 0, and the oxygen atoms are in the 1,2 positions |
| 120 | Formula VII wherein y = 0; hydroxyl groups are in the o,o' position | 2/1 | 75.7 | 4.13 | 75.3 | 4.71 | Formula XIV[2], y = 0, x = 0, and the bridging is in the o,o' position |
| 121 | Formula I wherein R = 2-OH; X = 4,t-butyl; y = 1 | 1/1 | 55.2 | 8.11 | 55.9 | 7.92 | Formula X[2]; X = 4-t-butyl; y = 1; m' = 1; n' = 2 |
| 122 | Formula II wherein n = 0; y = 0; bridging is o,o' | 1/1 | 60.2 | 6.45 | 60.6 | 5.91 | Formula XI wherein n = 0; y = 0; m' = 1; n' = 2; and the bridging is in the o,o' positions |

FOOTNOTES TO TABLE IX
[1]Compound or complex isolated as the hemihydrate.
[2]Compound or complex isolated as the monohydrate.

We claim:
1. A titanium complex or compound resulting from reacting
 (A) at least one titanium compound represented by the formula $Ti(OR)_xX_{4-x}$ wherein each R is independently a hydrocarbyl group having from 1 to about 20 carbon atoms; X is a halogen and x has a value from zero to 4; with
 (B) at least one compound containing at least one aromatic hydroxyl group represented by the formulas

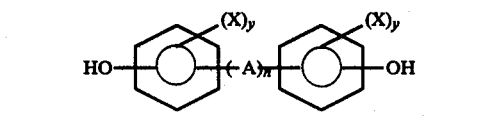

II.

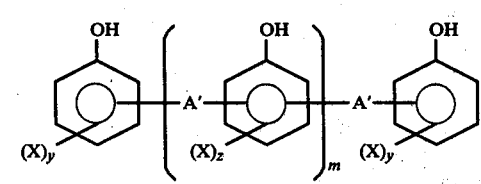

III.

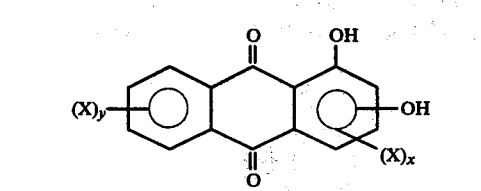

VI.

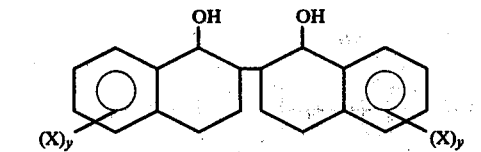

VII.

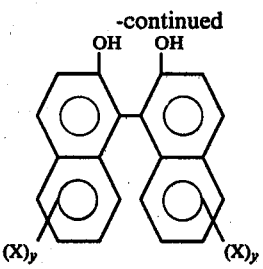

VIII.

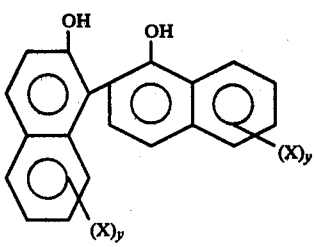

IX.

wherein each A is independently,

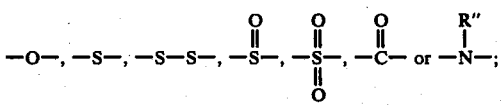

each A' is independently a divalent hydrocarbyl group having from 1 to about 10 carbon atoms; each R is independently

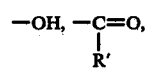

or a hydroxyl substituted hydrocarbyl or hydroxyl substituted hydrocarbyloxy group having from 1 to about 20 carbon atoms; each R' is independently hydrogen, hydroxyl or a hydrocarbyl or hydrocarbyloxy group having from 1 to about 10 carbon atoms; each R" is independently hydrogen or a hydrocarbyl group having from 1 to about 10 carbon atoms; each X is independently a hydroxyl group, a nitro group, a nitrile group, a hydrocarbyl group, a hydrocarbyloxy group, a hydroxyl substituted hydrocarbyl or a hydroxyl substituted hydrocarbyloxy group each such groups having from 1 to about 20 carbon atoms or a halogen; m has an average value of from about 0.01 to about 6; n has a value of 1; each x independently has a value of zero to 2; each y independently has a value of from zero to 4, and z has a value of from zero to 3; and wherein components (A) and (B) are employed in quantities which provides a molar ratio of B:A of from about 0.1:1 to about 10:1.

2. A titanium compound or complex of claim 1 wherein
(1) in component (A)
 (a) R has from about 1 to about 10 carbon atoms; and
 (b) X is chlorine;
(2) in component (B)
 (a) when A' is a divalent hydrocarbyl group it has from about 1 to about 4 carbon atoms;
 (b) when R is a hydroxyl substituted hydrocarbyl or a hydroxyl substituted hydrocarbyloxy group, it has from 1 to about 10 carbon atoms;
 (c) when R' is a hydrocarbyl group, it has from about 1 to about 6 carbon atoms;
 (d) when X is hydrocarbyl or hydrocarbyloxy, it has from about 1 to about 12 carbon atoms;
 (e) m has a value of from about 1 to about 3;
 (f) y has a value of from zero to 2;
 (g) z has a value from 1 to 2;
 (h) x has a value of zero; and
(3) components (A) and (B) are employed in quantities which provides a molar ratio of B:A of from about 1:1 to about 4:1.

3. A titanium compound or complex of claim 2 wherein
(a) in component (A), each R has from about 2 to about 4 carbon atoms,
(b) component (B) is represented by the formula

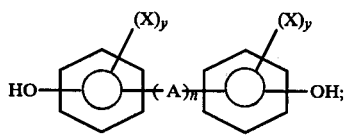
II.

and
(c) wherein components (A) and (B) are employed in quantities which provide a molar ratio of B:A of from about 1:1 to about 2:1.

4. A titanium compound or complex of claim 3 wherein in component (B) n has a value of 1 and A is

and the hydroxyl groups are in the ortho (2) position.

5. A titanium compound or complex of claim 4 wherein in component (B) each X is independently a hydrocarbyl group or a halogen and each y has a value of 1 or 2.

6. A titanium compound or complex of claim 5 wherein in component (B) each X is independently methyl or t-butyl and y has a value of 2.

7. A titanium compound or complex of claim 6 wherein in component (B) each X is t-butyl located at positions 3 and 5.

8. A titanium compound or complex of claim 5 wherein in component (B) A is

each X is independently chlorine, methyl or t-butyl and each y has a value of 2.

9. A titanium compound or complex of claim 8 wherein
(a) one X is t-butyl at position 3 and the other X is methyl at position 5; and
(b) each X is t-butyl, one at position 3 and the other at position 5.

10. A titanium compound or complex of claim 5 wherein in component (B) each X is chlorine in position 5 and each y has a value of 1.

11. A titanium compound or complex of claim 4 wherein y is zero.

12. A titanium compound or complex of claim 3 wherein in component (B) and the hydroxyl groups are in the ortho (2) position.

13. A titanium compound or complex of claim 2 wherein
(a) in component (A), each R has from about 2 to about 4 carbon atoms,
(b) component (B) is represented by the formula

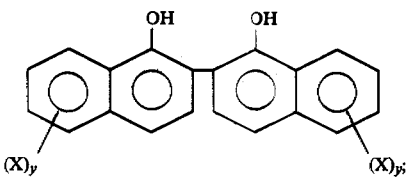
VII.

and
(c) components (A) and (B) are employed in quantities which provide a molar ratio of B:A of from about 1:1 to about 2:1.

14. A titanium compound or complex of claim 2 wherein
(1) in component (A), each R independently has from about 2 to about 4 carbon atoms; and
(2) component (B) is two different components each independently represented by the formulas

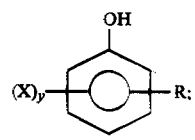

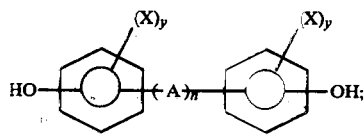
I.

-continued

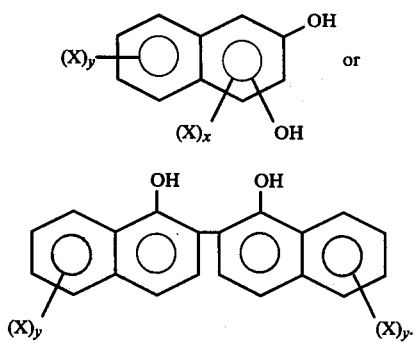

15. A titanium compound or complex of claim 14 wherein in component (B)
(a) one component is represented by formula I wherein R is OH, y has a value of zero and the other component is represented by formula I wherein R is OH, X is a hydrocarbyl group and y has a value of 1;
(b) one component is represented by formula I wherein R is OH, X is a hydrocarbyl group and y is 1 and the other component is represented by formula II wherein n is zero and the hydroxyl groups are in the ortho (2) position; or
(c) one component is represented by formula I wherein R is OH, X is a hydrocarbyl group and y is 1 and the other is represented by formula II wherein A is

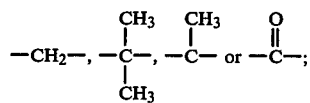

each X is independently a hydrocarbyl group, each y is 2, and n is 1; and
wherein components (A) and (B) are employed in quantities which provide a molar ratio of B:A of from about 1:1 to about 2:1.

16. A titanium compound or complex of claim 14 wherein in component (B)
(a) one component is represented by formula I wherein R is a hydroxyl group at position 2 and y has a value of zero and the other component is represented by formula I wherein R is a hydroxyl group at position 2, X is t-butyl at position 4 and y has a value of 1;
(b) one component is represented by formula I wherein R is a hydroxyl group at position 2, X is a t-butyl group at position 4, and y has a value of 1 and the other component is represented by the formula I wherein R is a hydroxyl group at position 2, each X is a t-butyl group, one at position 3 and the other at position 5 and y has a value of 2;
(c) one component is represented by formula I wherein R is a hydroxyl group at position 2, X is t-butyl at position 4 and y has a value of 1; and the other component is represented by formula II wherein n is zero and the hydroxyl groups are in the ortho (2) position and y has a value of zero; and
(d) one component is represented by formula I wherein R is a hydroxyl group at position 2, X is t-butyl at position 4 and y has a value of 1; and the other component is represented by formula II wherein A is

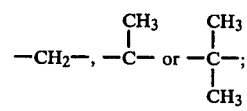

n is 1, one X is methyl at position 5, the other X is t-butyl at position 3 and y has a value of 2; and
wherein components (A) and (B) are employed in quantities which provide a molar ratio of B:A of from about 1:1 to about 2:1.

17. A titanium compound or complex of claims 1, 2, 3, 4, 5, 6, 7, 8, 9, 10, 11, 12, 13, 14, 15 or 16 wherein component (A) is tetraisopropoxy titaium; tetra-n-butoxy titanium; titanium tetrachloride or a mixture thereof.

18. In a Zeigler-Natta catalyst containing a titanium component; the improvenent which comprises employing as the titanium component that which results from reacting
(A) at least one titanium compound represented by the formula $Ti(OR)_xX_{4-x}$ wherein each R is independently a hydrocarbyl group having from 1 to about 20 carbon atoms; X is a halogen and x has a value from zero to 4; with
(B) at least one compound containing at least one aromatic hydroxyl group represented by the formulas

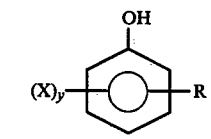  I.

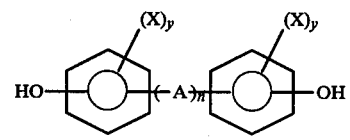  II.

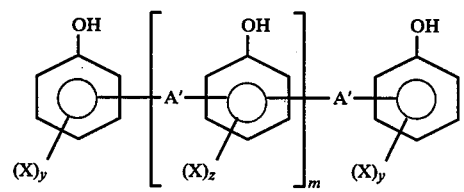  III.

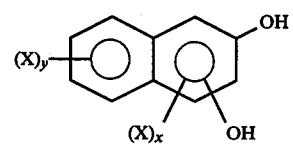  IV.

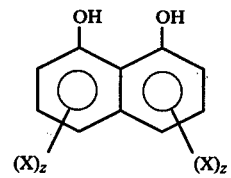  V.

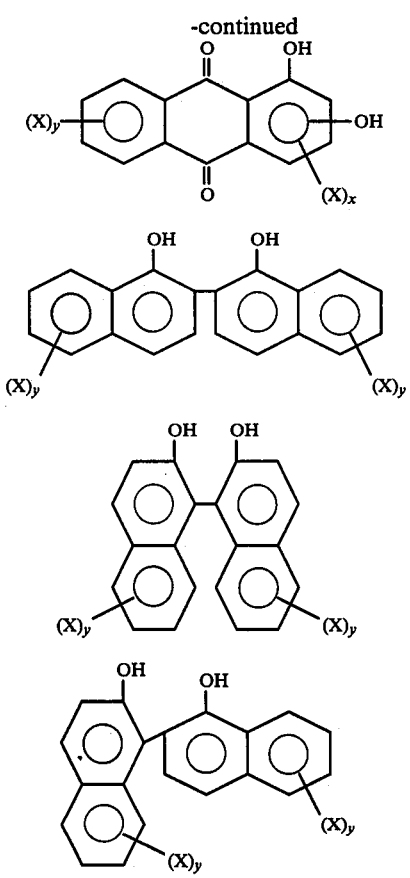

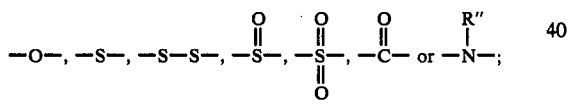

wherein each A is independently a divalent hydrocarbyl group having from 1 to about 10 carbon atoms, $$-O-, \ -S-, \ -S-S-, \ -\underset{\underset{O}{\|}}{\overset{\overset{O}{\|}}{S}}-, \ -\overset{O}{\underset{\|}{S}}-, \ -\overset{O}{\underset{\|}{C}}- \text{ or } -\overset{R''}{\underset{|}{N}}-;$$

each A' is independently a divalent hydrocarbyl group having from 1 to about 10 carbon atoms; each R is independently

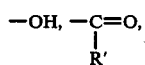

or a hydroxyl substituted hydrocarbyl or hydroxyl substituted hydrocarbyloxy group having from 1 to about 20 carbon atoms; each R' is independently hydrogen, hydroxyl or a hydrocarbyl or hydrocarbyloxy group having from 1 to about 10 carbon atoms; each R'' is independently hydrogen or a hydrocarbyl group having from 1 to about 10 carbon atoms; each X is independently a hydroxyl group, a nitro group, a nitrile group, a hydrocarbyl group, a hydrocarbyloxy group, a hydroxyl substituted hydrocarbyl or a hydroxyl substituted hydrocarbyloxy group each such groups having from 1 to about 20 carbon atoms or a halogen; m has an average value of from about 0.01 to about 6; each n independently has a value of zero or 1; each X independently has a value of zero to 2; each y independently has a value of from zero to 4, and z has a value of from zero to 3; and wherein components (A) and (B) are employed in quantities which provides a molar ratio of B:A of from about 0.1:1 to about 10:1.

19. A Ziegler-Natta catalyst of claim 18 wherein
(1) in component (A)
 (a) each R independently has from about 1 to about 10 carbon atoms; and
 (b) X is chlorine;
(2) in component (B)
 (a) when A is a divalent hydrocarbyl group, it has from about 1 to about 4 carbon atoms;
 (b) when A' is a divalent hydrocarbyl group it has from about 1 to about 4 carbon atoms;
 (c) when R is a hydroxyl substituted hydrocarbyl or a hydroxyl substituted hydrocarbyloxy group, it has from 1 to about 10 carbon atoms;
 (d) when R' is a hydrocarbyl group, it has from about 1 to about 6 carbon atoms;
 (e) when X is hydrocarbyl or hydrocarbyloxy, it has from about 1 to about 12 carbon atoms;
 (f) m has a value of from about 1 to about 3;
 (g) y has a value from zero to 2;
 (h) z has a value from 1 to 2; and
 (i) x has a value of zero; and
(3) components (A) and (B) are employed in quantities which provides a molar ratio of B:A of from about 1:1 to about 4:1.

20. A Ziegler-Natta catalyst of claim 19 wherein
(A) in component (A), each R independently has from about 2 to about 4 carbon atoms;
(B) component (B) is represented by the formula

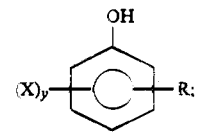

and
(C) components (A) and (B) are employed in quantities which provide a molar ratio of B:A of from about 1:1 to about 2:1.

21. A Ziegler-Natta catalyst of claim 20 wherein in component (B)
 (A) R is —OH and
 (B) each X is independently hydrocarbyl, hydrocarbyloxy, halogen, nitrile, nitro, formyl or carboxyl.

22. A Ziegler-Natta catalyst of claim 21 wherein in component (B) each X is independently chlorine, methyl, isopropyl, t-butyl, t-octyl or methoxy.

23. A Ziegler-Natta catalyst of claim 22 wherein in component (B) y has a value of 1 and X is t-butyl, t-octyl, methoxy or chlorine.

24. A Ziegler-Natta catalyst of claim 23 wherein component (B) is 4-t-butyl catechol.

25. A Ziegler-Natta catalyst of claim 21 wherein in component (B) y has a value of 2 and each X is the same and is t-butyl or t-octyl.

26. A Ziegler-Natta catalyst of claim 22 wherein in component (B) y has a value of 2 and
 (a) one X is isopropyl in position 3 and the other is methyl in position 6, or
 (b) each X is t-butyl, one being at position 3 and the other at position 5.

27. A Ziegler-Natta catalyst of claim 19 wherein (a) in component (A), each R has from about 2 to about 4 carbon atoms;

(b) component (B) is represented by the formula

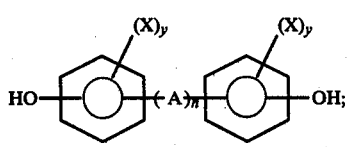

and (c) components (A) and (B) are employed in quantities which provide a molar ratio of B:A of from about 1:1 to about 2:1.

28. A Ziegler-Natta catalyst of claim 27 wherein in component (B) n has a value of 1 and A is

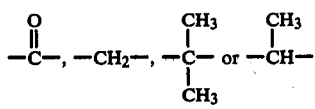

and the hydroxyl groups are in the ortho (2) position.

29. A Ziegler-Natta catalyst of claim 28 wherein in component (B) each X is independently a hydrocarbyl group or a halogen and each y has a value of 1 or 2.

30. A Ziegler-Natta catalyst of claim 29 wherein in component (B) A is

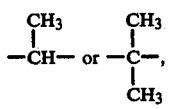

each X is independently methyl or t-butyl and y has a value of 2.

31. A Ziegler-Natta catalyst of claim 30 wherein in component (B) each X is t-butyl located at positions 3 and 5.

32. A Ziegler-Natta catalyst of claim 28 wherein in component (B) A is

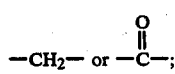

each X is independently chlorine, methyl or t-butyl and each y has a value of 2.

33. A Ziegler-Natta catalyst of claim 32 wherein
(a) one X is t-butyl at position 3 and the other X is methyl at position 5; and
(b) each X is t-butyl, one at position 3 and the other at position 5.

34. A Ziegler-Natta catalyst of claim 29 wherein in component (B) A is —CH$_2$— and each X is chlorine in position 5 and each y has a value of 1.

35. A Ziegler-Natta catalyst of claim 28 wherein A is —CH$_2$— and y is zero.

36. A Ziegler-Natta catalyst of claim 27 wherein in component (B) n has a value of zero and the hydroxyl groups are in the ortho (2) position.

37. A Ziegler-Natta catalyst of claim 19 wherein
(1) in component (A), each R independently has from about 2 to about 4 carbon atoms, and
(2) component (B) is two different components each independently represented by the formulas

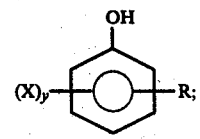

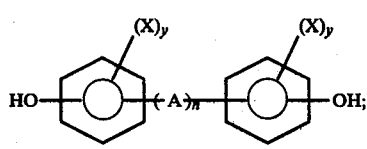

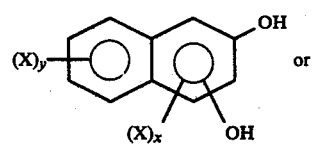

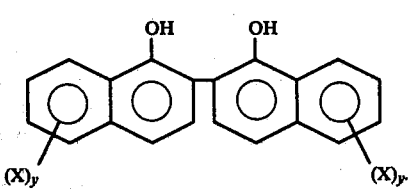

38. A Ziegler-Natta catalyst of claim 37 wherein in component B
(a) one component is represented by formula I wherein R is OH, y has a value of zero and the other component is represented by formula I wherein R is OH, X is a hydrocarbyl group and y has a value of 1;
(b) one component is represented by formula I wherein R is OH, X is a hydrocarbyl group and y is 1 and the other component is represented by formula II wherein n is zero and the hydroxyl groups are in the ortho (2) position; or
(c) one component is represented by formula I wherein R is OH, X is a hydrocarbyl group and y is 1 and the other is represented by formula II wherein A is

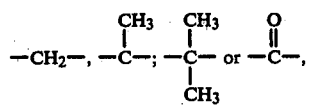

each X is independently a hydrocarbyl group, each y is 2, and n is 1; and
wherein components (A) and (B) are employed in quantities which provide a molar ratio of B:A of from about 1:1 to about 2:1.

39. A Ziegler-Natta catalyst of claim 37 wherein in component (B)
(a) one component is represented by formula I wherein R is a hydroxyl group at position 2 and y has a value of zero and the other component is represented by formula I wherein R is a hydroxyl group at position 2, X is t-butyl at position 4 and y has a value of 1;
(b) one component is represented by formula I wherein R is a hydroxyl group at position 2, X is a t-butyl group at position 4, and y has a value of 1 and the other component is represented by the formula I wherein R is a hydroxyl group at position 2, each X is a t-butyl group, one at position 3 and the other at position 5 and y has a value of 2;

(c) one component is represented by formula I wherein R is a hydroxyl group at position 2, X is t-butyl at position 4 and y has a value of 1; and the other component is represented by formula II wherein n is zero and the hydroxyl groups are in the ortho (2) position and y has a value of zero; and (d) one component is represented by formula I wherein R is a hydroxyl group at position 2, X is t-butyl at position 4 and y has a value of 1; and the other component is represented by formula II wherein A is

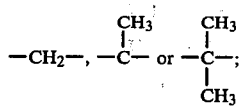

n is 1, one X is methyl at position 5, the other X is t-butyl at position 3 and y has a value of 2; and wherein components (A) and (B) are employed in quantities which provide a molar ratio of B:A of from about 1:1 to about 2:1.

40. A Ziegler-Natta catalyst of claims 18, 19, 20, 21, 22, 23, 24, 25, 26, 27, 28, 29, 30, 31, 32, 33, 34, 35, 36, 37, 38 or 39 wherein component (A) is tetraiisopropoxy titanium, tetra-n-butoxy titanium, titanium tetrachloride or a mixture thereof.

41. A catalyst composition resulting from reacting in an inert hydrocarbon medium (A) at least one hydrocarbon soluble organomagnesium component represented by the formula $MgR''_2 \cdot xMR''_y$ wherein each $R''$ is independently a hydrocarbyl group having from 1 to 20 carbon atoms; M is a metal selected from Al, Zn, Si, Sn, B and P; y has a number corresponding to the valence of M and x has a value from about 0.001 to about 10;

(B) a sufficient quantity of at least one halide source so as to convert all of the organic groups attached to a magnesium atom in component (A) to a halide group; said halide source being selected from (1) an active non-metallic halide, said non-metallic halide corresponding to the formula R'X wherein R' is hydrogen or a hydrocarbyl group having from 1 to about 20 carbon atoms and such that the hydrocarbyl halide is at least as active as sec-butyl chloride and does not poison the catalyst and X is halogen; or (2) a metallic halide corresponding to the formula $MR_{y-a}X_a$ wherein M is a metal of Group IIIA or IVA of Mendeleev's Periodic Table of Elements, R is a monovalent hydrocarbyl group having from 1 to about 20 carbon atoms, X is halogen, y is a number corresponding to the valence of M and a is a number from 1 to y;

(C) at least one titanium compound represented by the formula $Ti(OR)_xX_{4-x}$ wherein each R is independently a hydrocarbyl group having from 1 to about 20 carbon atoms; X is a halogen and x has a value from zero to 4; with (D) at least one compound containing at least one aromatic hydroxyl group represented by the formulas

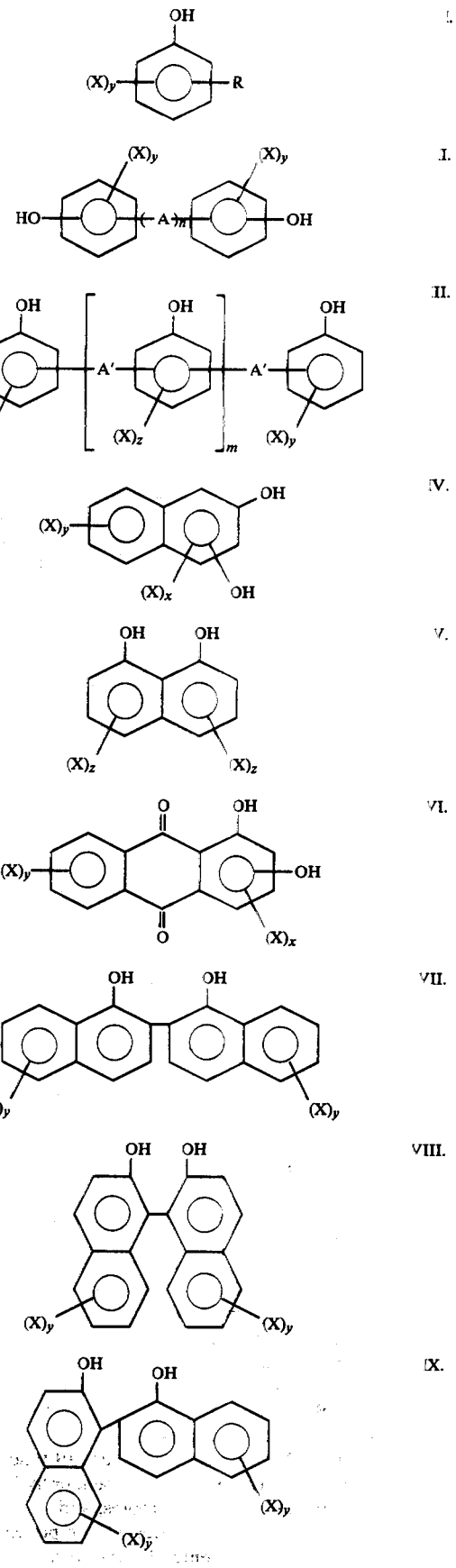

wherein each A is independently a divalent hydrocarbyl group having from 1 to about 10 carbon atoms,

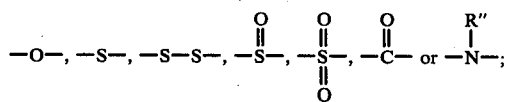

each A' is independently a divalent hydrocarbyl group having from 1 to about 10 carbon atoms; each R is independently

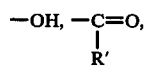

or a hydroxyl substituted hydrocarbyl or hydrocarbyloxy group having from 1 to about 20 carbon atoms; each R' is independently hydrogen, hydroxyl or a hydrocarbyl or hydrocarbyloxy group having from 1 to about 10 carbon atoms; each R'' is independently hydrogen or a hydrocarbyl group having from 1 to about 10 carbon atoms; each X is independently a hydroxyl group, a nitro group, a nitrile group, a hydrocarbyl group, a hydrocarbyloxy group, a hydroxyl substituted hydrocarbyl or a hydroxyl substituted hydrocarbyloxy group each such groups having from 1 to about 20 carbon atoms or a halogen; m has an average value of from about 0.01 to about 6; each n independently has a value of zero or 1; each x independently has a value of zero or 1; each y independently has a value of from zero to 4, and z has a value of from zero to 3; and when components (A) and/or (C) do not contain or contain an insufficient quantity of aluminum, then (E) an aluminum compound represented by the formula $AlR_{y'}X_{y''}$ wherein R is a hydrocarbyl group having from 1 to about 10 carbon atoms; X is halogen and y' and y'' each have a value of from zero to three with the sum of y' and y'' being three is employed;

and wherein the components are employed in quantities so as to provide the following ratios:
(1) a Mg:Ti atomic ratio of from about 1:1 to about 200:1;
(2) components (C) and (D) are employed in quantities which provide a molar ratio of D:C of from about 0.1:1 to about 10:1;
(3) an excess X to Al ratio of from about 0.0005:1 to about 10:1; and
(4) an Al:Ti atomic ratio of from about 0.1:1 to about 2000:1.

42. A catalyst composition of claim 41 wherein
(1) in component (A),
(a) R'' has from 1 to about 10 carbon atoms;
(b) M is aluminum; and
(c) x has a value from 0.001 to about 5;
(2) in component (B),
(a) M is aluminum;
(b) R' is hydrogen or a tertiary butyl group;
(c) X is chlorine; and
(d) R and R' independently have from 1 to about 10 carbon atoms;
(3) in component (C),
(a) R has from about 1 to about 10 carbon atoms; and
(b) X is chlorine;

(4) in component (D)
(a) when A is a divalent hydrocarbyl group, it has from about 1 to about 4 carbon atoms;
(b) when A' is a divalent hydrocarbyl group it has from about 1 to about 4 carbon atoms;
(c) when R is a hydroxyl substituted hydrocarbyl or a hydroxyl substituted hydrocarbyloxy group, it has from 1 to about 10 carbon atoms;
(d) when R' is a hydrocarbyl group, it has from about 1 to about 6 carbon atoms;
(e) when X is hydrocarbyl or hydrocarbyloxy, it has from about 1 to about 12 carbon atoms;
(f) m has a value of from about 1 to about 3;
(g) y has a value from zero to 2;
(h) z has a value from 1 to 2; and
(i) x has a value of zero;
(5) in component (E),
(a) M is aluminum;
(b) R has from 1 to about 10 carbon atoms; and
(c) X is chlorine; and
(6) the components are employed in quantities so as to provide the following ratios:
(a) a Mg:Ti atomic ratio of from about 2:1 to about 100:1;
(b) components (C) and (D) are employed in quantities which provide a molar ratio of D:C of from about 1:1 to about 4:1;
(c) an excess X to Al ratio of from about 0.002:1 to about 2:1; and
(d) an Al:Ti atomic ratio of from about 0.5:1 to about 200:1.

43. A catalyst composition of claim 42 wherein
(a) in component (C), each R independently has from about 2 to about 4 carbon atoms; and
(b) component (D) is represented by the formula

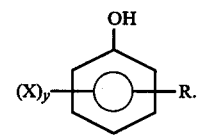

44. A catalyst composition of claim 43 wherein the components are employed in quantities so as to provide the following ratios:
(a) a Mg:Ti atomic ratio of from about 5:1 to about 50:1;
(b) components (C) and (D) are employed in quantities which provide a molar ratio of D:C of from about 1:1 to about 2:1;
(c) an excess X to Al ratio of from about 0.01:1 to about 1.4:1; and
(d) an Al:Ti atomic ratio of from about 1:1 to about 75:1.

45. A catalyst composition of claim 44 wherein in component (D) each X is independently chlorine, methyl, isopropyl, t-butyl, t-octyl or methoxy.

46. A catalyst composition of claim 45 wherein in component (D) y has a value of 1 and X is t-butyl, t-octyl, methoxy or chlorine.

47. A catalyst composition of claim 46 wherein component (D) is 4-t-butyl catechol.

48. A catalyst composition of claim 45 wherein in component (D) y has a value of 2 and each X is the same and is t-butyl or t-octyl.

49. A catalyst composition of claim 45 wherein in component (D) y has a value of 2 and (a) one X is isopropyl in position 3 and the other is methyl in position 6, or (b) each X is t-butyl, one being at position 3 and the other at position 5.

50. A catalyst composition of claim 42 wherein
(A) in component (C), each R independently has from about 2 to about 4 carbon atoms; and
(B) component (D) is represented by the formula

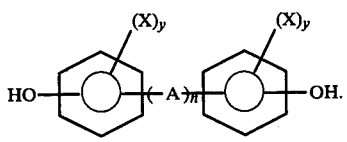
II.

51. A catalyst composition of claim 49 wherein the components are employed in quantities so as to provide the following ratios:

(a) a Mg:Ti atomic ratio of from about 5:1 to about 50:1;
(b) components (C) and (D) are employed in quantities which provide a molar ratio of D:C of from about 1:1 to about 2:1;
(c) an excess X to Al ratio of from about 0.01:1 to about 1.4:1; and
(d) an Al:Ti atomic ratio of from about 1:1 to about 75:1.

52. A catalyst composition of claim 51 wherein in component (D) n has a value of 1 and A is

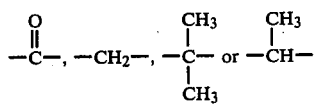

and the hydroxyl groups are in the ortho (2) position.

53. A catalyst composition of claim 52 wherein in component (D) each X is independently a hydrocarbyl group or a halogen and each y has a value of 1 or 2.

54. A catalyst composition of claim 53 wherein in component (D) A is

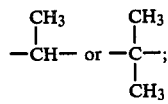

each X is independently methyl or t-butyl and y has a value of 2.

55. A catalyst composition of claim 54 wherein in component (D) each X is t-butyl located at positions 3 and 5.

56. A catalyst composition of claim 53 wherein in component (D) A is

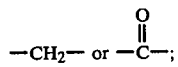

each X is independently chlorine, methyl or t-butyl and each y has a value of 2.

57. A catalyst composition of claim 56 wherein in component (D)

(A) one X is t-butyl at position 3 and the other X is methyl at position 5; or
(B) each X is t-butyl, one at position 3 and the other at position 5.

58. A catalyst composition of claim 53 wherein in component (D) A is —$CH_2$— and each X is chlorine in position 5 and each y has a value of 1.

59. A catalyst composition of claim 52 wherein A is —$CH_2$— and y is zero.

60. A catalyst composition of claim 51 wherein in component (D) n has a value of zero and the hydroxyl groups are in the ortho (2) positions.

61. A catalyst composition of claim 42 wherein
(a) in component (A), each R has from about 2 to about 4 carbon atoms,
(b) component (B) is represented by the formula

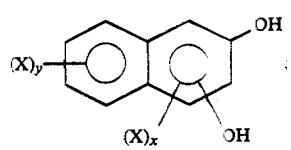
V.

and
(c) components (A) and (B) are employed in quantities which provide a molar ratio of B:A of from about 1:1 to about 2:1.

62. A catalyst composition of claim 42 wherein
(a) in component (A), each R has from about 2 to about 4 carbon atoms,
(b) component (B) is represented by the formula

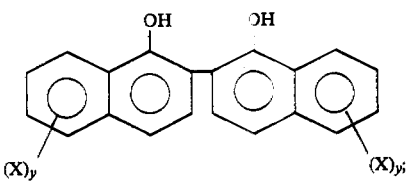
VI.

and
(c) components (A) and (B) are employed in quantities which provide a molar ratio of B:A of from about 1:1 to about 2:1.

63. A catalyst composition of claim 42 wherein
(A) in component (C), each R independently has from about 2 to about 4 carbon atoms; and
(B) component (D) is two different components each independently represented by the formulas

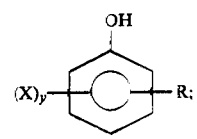

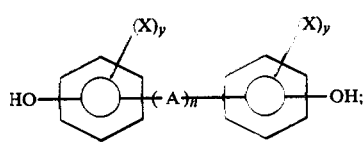
I.

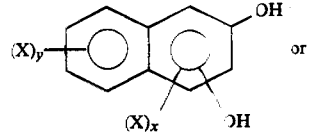
V.
or

-continued

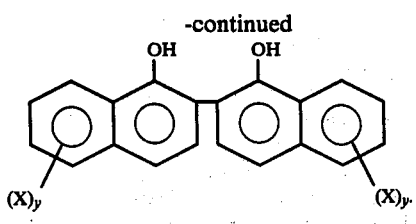                VII.

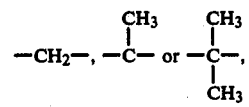

64. A catalyst composition of claim 63 wherein in component D
(a) one component is represented by formula I wherein R is OH, y has a value of zero and the other component is represented by formula I wherein R is OH, X is a hydrocarbyl group and y has a value of 1;
(b) one component is represented by formula I wherein R is OH, X is a hydrocarbyl group and y is 1 and the other component is represented by formula II wherein n is zero and the hydroxyl groups are in the ortho (2) position; or
(c) one component is represented by formula I wherein R is OH, X is a hydrocarbyl group and y is 1 and the other is represented by formula II wherein A is

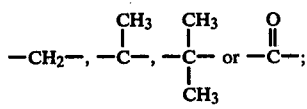

each X is independently a hydrocarbyl group, each y is 2, and n is 1; and
wherein components (A) and (B) are employed in quantities which provide a molar ratio of B:A of from about 1:1 to about 2:1.

65. A catalyst composition of claim 63 wherein in component (D)
(A) one component is represented by formula I wherein R is a hydroxyl group at position 2 and y has a value of zero and the other component is represented by formula I wherein R is a hydroxyl group at position 2, X is t-butyl at position 4 and y has a value of 1;
(B) one component is represented by formula I wherein R is a hydroxyl group at position 2, X is a t-butyl group at position 4, and y has a value of 1 and the other component is represented by the formula I wherein R is a hydroxyl group at position 2, each X is a t-butyl group, one at position 3 and the other at position 5 and y has a value of 2;
(C) one component is represented by formula I wherein R is a hydroxyl group at position 2, X is t-butyl at position 4 and y has a value of 1; and the other component is represented by formula II wherein n is zero and the hydroxyl groups are in the ortho (2) position and y has a value of zero; and
(D) one component is represented by formula I wherein R is a hydroxyl group at position 2, X is t-butyl at position 4 and y has a value of 1; and the other component is represented by formula II wherein A is n is 1, one X is methyl at position 5, the other X is t-butyl at position 3 and y has a value of 2; and
wherein components (A) and (B) are employed in quantities which provide a molar ratio of B:A of from about 1:1 to about 2:1.

66. A catalyst composition of claims 41, 42, 43, 44, 45, 46, 47, 48, 49, 50, 51, 52, 53, 54, 55, 56, 57, 58, 59, 60, 61, 62, 63, 64 or 65 wherein the components are added in the order selected from
(A) A, B, (C and D, prereacted), E (if required);
(B) A, B, E (if required), (C and D, prereacted);
(C) (A and B, prereacted), (C and D, prereacted), E (if required);
(D) (A and B, prereacted), E (if required), (C and D, prereacted); or
(E) (A, B, and E (if required), prereacted), (C and D, prereacted).

67. A catalyst composition of claims 41, 42, 43, 44, 45, 46, 47, 48, 49, 50, 51, 52, 53, 54, 55, 56, 57, 58, 59, 60, 61, 62, 63, 64 or 65 wherein component (C) is tetraisopropoxy titanium, tetra-n-butoxy titanium, titanium tetrachloride or a mixture thereof.

68. A catalyst composition of claim 66 wherein component (C) is tetraiisopropoxy titanium, tetra-n-butoxy titanium, titanium tetrachloride or a mixture thereof.

69. A bidentate ligand-containing titanium compound or complex represented by the formulas

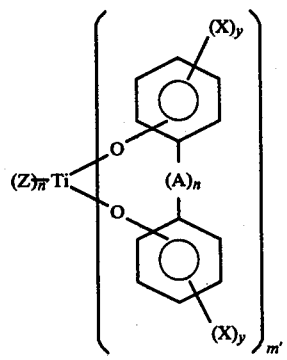    XI.

wherein each A is independently

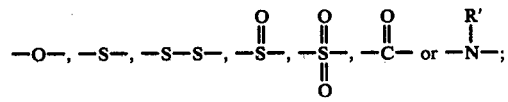

each X is independently a hydroxyl group, a nitro group a nitrile group, a hydrocarbyl group, a hydrocarbyloxy group, a hydroxyl substituted hydrocarbyl or a hydroxyl substituted hydrocarbyloxy group each such groups having from 1 to about 20 carbon atoms or a halogen; each Z is independently a halogen or an $R^2O$—group, each $R^2$ is independently a hydrocarbyl group having from 1 to about 20 carbon atoms; n has a value of 1; m' has a value of 1 or 2; n' has a value of zero when m' has a value of 2 and a value of 2 when m' has a value of 1; and y has a value from zero to 4;

XIII.

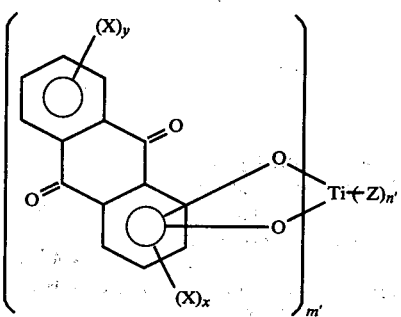

wherein each $R^2$, X, Z, m', n', y and x are as defined above; or

XIV.

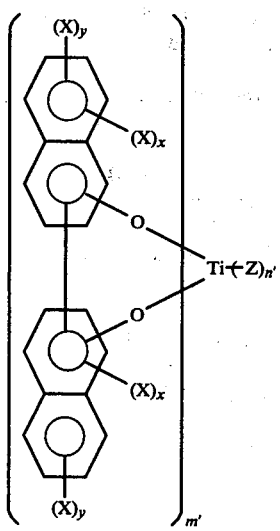

wherein each $R^2$, X, Z, m', n', x and y are as defined above.

70. A bidentate ligand-containing titanium compound or complex of claim 69 wherein each $R^2$ has from 1 to about 10 carbon atoms; and when X is a hydrocarbyl, hydrocarbyloxy, hydroxyl substituted hydrocarbyl or hydroxyl substituted hydrocarbyloxy, each such group has from 1 to about 10 carbon atoms.

71. A bidentate ligand-containing compound or complex of claim 70 represented by Formula XI wherein A is —$CH_2$—; n=1, X is 3,3'-di-t-butyl and 5,5'-dimethyl; bridging is in the o,o' positions, m'=2, n'=0 and y=2.

72. A bidentate ligand-containing compound or complex of claim 70 represented by Formula XIII wherein x=0, y=0, m'=2, n'=0 and the oxygen atoms are in the 1 and 2 positions.

73. A bidentate ligand-containing compound or complex of claim 72 which is in the form of a monohydrate.

74. A bidentate ligand-containing compound or complex of claim 70 represented by Formula XIV wherein y=0, x=0, the bridging is in the 1,1' positions, m'=2 and n'=0 and the oxygen atoms are in positions 2 and 2'.

75. A bidentate ligand-containing compound or complex of claim 74 which is in the form of a monohydrate.

* * * * *